US009795751B2

(12) United States Patent
Bilgic

(10) Patent No.: US 9,795,751 B2
(45) Date of Patent: Oct. 24, 2017

(54) DRY POWDER INHALER

(71) Applicant: Sima Patent ve Lisanslama Hizmetleri Ltd. Sti., Esenler/Istanbul (TR)

(72) Inventor: Mahmut Bilgic, Istanbul (TR)

(73) Assignee: Sima Patent ve Lisanslama Hizmetleri Ltd. Sti., Esenler/Istanbul (TR)

( * ) Notice: Subject to any disclaimer, the term of this patent is extended or adjusted under 35 U.S.C. 154(b) by 270 days.

(21) Appl. No.: 14/695,739

(22) Filed: Apr. 24, 2015

(65) Prior Publication Data

US 2015/0231346 A1 Aug. 20, 2015

Related U.S. Application Data

(60) Division of application No. 13/451,838, filed on Apr. 20, 2012, now Pat. No. 9,345,848, which is a
(Continued)

(30) Foreign Application Priority Data

Oct. 20, 2009 (TR) .................................. 2009/07917
Apr. 13, 2010 (TR) .................................. 2010/02877
(Continued)

(51) Int. Cl.
*A61M 15/00* (2006.01)
(52) U.S. Cl.
CPC .... *A61M 15/0053* (2014.02); *A61M 15/0025* (2014.02); *A61M 15/0046* (2014.02);
(Continued)

(58) Field of Classification Search
CPC .......... A61M 15/0003; A61M 15/0006; A61M 15/0008; A61M 15/0013; A61M 15/0016;
(Continued)

(56) References Cited

U.S. PATENT DOCUMENTS

| 2,625,292 A | 1/1953 | Spender |
| D335,029 S | 4/1993 | Gerding |

(Continued)

FOREIGN PATENT DOCUMENTS

| CA | 2544745 A1 | 5/2005 |
| EP | 1175220 A2 | 1/2002 |

(Continued)

OTHER PUBLICATIONS

International Search Report and Written Opinion for International Application No. PCT/TR2011/000085 dated Aug. 10, 2011 (10 pages).

(Continued)

*Primary Examiner* — Annette Dixon
(74) *Attorney, Agent, or Firm* — Clark & Elbing LLP

(57) ABSTRACT

The present invention relates to an inhaler which is appropriate for delivery of medicament in dry powder form used in respiratory diseases, particularly in asthma and chronic obstructive pulmonary disease (COPD). In addition, the present invention relates to an inhaler which includes a blister package appropriate for carrying the medicament in dry powder form and used to realize an effective inhalation.

31 Claims, 29 Drawing Sheets

Related U.S. Application Data continuation-in-part of application No. PCT/TR2011/000091, filed on Apr. 13, 2011, and a continuation-in-part of application No. PCT/TR2011/000094, filed on Apr. 13, 2011, and a continuation-in-part of application No. PCT/TR2011/000089, filed on Apr. 13, 2011, and a continuation-in-part of application No. PCT/TR2011/000093, filed on Apr. 13, 2011, and a continuation-in-part of application No. PCT/TR2011/000085, filed on Apr. 13, 2011, and a continuation-in-part of application No. PCT/TR2011/000088, filed on Apr. 13, 2011, and a continuation-in-part of application No. PCT/TR2011/000087, filed on Apr. 13, 2011, and a continuation-in-part of application No. PCT/TR2011/000095, filed on Apr. 13, 2011, and a continuation-in-part of application No. PCT/TR2011/000086, filed on Apr. 13, 2011, and a continuation-in-part of application No. PCT/TR2011/000090, filed on Apr. 13, 2011, and a continuation-in-part of application No. PCT/TR2010/000210, filed on Oct. 20, 2010.

(30) Foreign Application Priority Data

| Apr. 20, 2010 | (TR) | 2010/03091 |
|---|---|---|
| Apr. 26, 2010 | (TR) | 2010/03238 |
| May 28, 2010 | (TR) | 2010/04307 |
| May 28, 2010 | (TR) | 2010/04308 |
| May 28, 2010 | (TR) | 2010/04310 |
| May 28, 2010 | (TR) | 2010/04312 |
| May 28, 2010 | (TR) | 2010/04313 |
| May 28, 2010 | (TR) | 2010/04317 |

(52) U.S. Cl.
CPC ... *A61M 15/0071* (2014.02); *A61M 2202/064* (2013.01); *A61M 2205/19* (2013.01)

(58) Field of Classification Search
CPC .......... A61M 15/0025; A61M 15/0026; A61M 15/0028; A61M 15/0031; A61M 15/0033; A61M 15/0036; A61M 15/0041; A61M 15/0043; A61M 15/0045; A61M 15/0048; A61M 15/0051; A61M 15/0055; A61M 15/006; A61M 15/0066; A61M 15/007; A61M 15/0075; A61M 15/0078; A61M 15/0085; A61M 15/0086; A61M 15/0091; A61M 15/02; A61M 16/127; A61M 2016/0024; A61M 2202/064; A61M 2205/073; A61M 2205/12; A61M 2205/123; A61M 2205/14; A61M 2205/18; A61M 2205/582; A61M 2205/583; A61M 2205/8206; A61M 2206/16

USPC ............ 128/200.23, 202.22, 203.12, 203.15, 128/203.21

See application file for complete search history.

(56) References Cited

U.S. PATENT DOCUMENTS

| 5,619,984 | A | * | 4/1997 | Hodson ............. A61M 15/0028 128/203.12 |
|---|---|---|---|---|
| 5,657,749 | A | | 8/1997 | Cox |
| 6,092,522 | A | | 7/2000 | Calvert et al. |
| 6,234,365 | B1 | | 5/2001 | Bougamont et al. |
| D450,117 | S | | 11/2001 | Braithwaite et al. |
| D479,689 | S | | 9/2003 | Altonen et al. |
| 6,880,555 | B1 | | 4/2005 | Brunnberg et al. |
| D505,865 | S | | 6/2005 | Seizer et al. |
| D518,171 | S | | 3/2006 | Anderson et al. |
| D590,495 | S | | 4/2009 | Lulla et al. |
| D590,938 | S | | 4/2009 | Lulla et al. |
| D613,397 | S | | 4/2010 | Nakao et al. |
| 7,694,676 | B2 | | 4/2010 | Wachtel |
| D641,890 | S | | 7/2011 | Nardo |
| D645,734 | S | | 9/2011 | Eason et al. |
| D683,844 | S | | 6/2013 | Andrade et al. |
| D710,002 | S | | 7/2014 | Valentine et al. |
| 2002/0132001 | A1 | | 9/2002 | Garthwaite et al. |
| 2003/0172927 | A1 | * | 9/2003 | Young ............... A61M 15/0045 128/203.15 |
| 2004/0094152 | A1 | | 5/2004 | Harvey et al. |
| 2004/0173211 | A1 | | 9/2004 | Kladders et al. |
| 2005/0005934 | A1 | | 1/2005 | Harvey |
| 2005/0154491 | A1 | | 7/2005 | Anderson et al. |
| 2005/0172964 | A1 | | 8/2005 | Anderson et al. |
| 2005/0268909 | A1 | | 12/2005 | Bonney et al. |
| 2005/0279357 | A1 | | 12/2005 | Wachtel |
| 2006/0196504 | A1 | | 9/2006 | Augustyn et al. |
| 2007/0062525 | A1 | | 3/2007 | Bonney et al. |
| 2008/0196718 | A1 | * | 8/2008 | Connell ............ A61M 15/0045 128/203.15 |
| 2008/0308102 | A1 | | 12/2008 | Davies et al. |
| 2009/0078252 | A1 | | 3/2009 | Anderson et al. |
| 2009/0139516 | A1 | * | 6/2009 | Augustyn ......... A61M 15/0045 128/200.23 |
| 2010/0000528 | A1 | | 1/2010 | Palmer et al. |
| 2010/0000529 | A1 | | 1/2010 | Prime et al. |
| 2010/0059052 | A1 | * | 3/2010 | Davies ................... A61J 1/035 128/203.15 |
| 2011/0232637 | A1 | | 9/2011 | Kaemper et al. |
| 2011/0271958 | A1 | | 11/2011 | Sawant |
| 2012/0260917 | A1 | | 10/2012 | Bilgic |
| 2014/0318538 | A1 | | 10/2014 | Bilgic |
| 2015/0231345 | A1 | | 8/2015 | Bilgic |
| 2015/0231346 | A1 | | 8/2015 | Bilgic |

FOREIGN PATENT DOCUMENTS

| EP | 2082759 A1 | 7/2009 |
|---|---|---|
| EP | 2082764 A1 | 7/2009 |
| GB | 1459426 A | 12/1976 |
| GB | 2407042 A | 4/2005 |
| GB | 2447560 A | 9/2008 |
| WO | WO-00/33847 A1 | 6/2000 |
| WO | WO-01/41770 A2 | 6/2001 |
| WO | WO-02/36189 A1 | 5/2002 |
| WO | WO-03/095010 A2 | 11/2003 |
| WO | WO-2006/066908 A1 | 6/2006 |
| WO | WO-2007/012960 A1 | 2/2007 |
| WO | WO-2008/074098 A1 | 6/2008 |
| WO | WO-2009/003989 A1 | 1/2009 |
| WO | WO-2009/139731 A1 | 11/2009 |
| WO | WO-2011/133740 A1 | 10/2011 |

OTHER PUBLICATIONS

International Search Report and Written Opinion for International Application No. PCT/TR2011/000086, dated Oct. 6, 2011 (8 pages).
International Search Report and Written Opinion for International Application No. PCT/TR2011/000087 dated Aug. 18, 2011 (8 pages).
International Search Report and Written Opinion for International Application No. PCT/TR2011/000088 dated Oct. 6, 2011 (8 pages).
International Search Report and Written Opinion for International Application No. PCT/TR2011/000089 dated Jul. 22, 2011 (9 pages).
International Search Report and Written Opinion for International Application No. PCT/TR2011/000090 dated Aug. 22, 2011 (8 pages).
International Search Report and Written Opinion for International Application No. PCT/TR2011/000091 dated Jul. 29, 2011 (9 pages).
International Search Report and Written Opinion for International Application No. PCT/TR2011/000093 dated Jul. 21, 2011 (9 pages).

(56) References Cited

OTHER PUBLICATIONS

International Search Report and Written Opinion for International Application No. PCT/TR2011/000094 dated Sep. 28, 2011 (9 pages).
International Search Report and Written Opinion for International Application No. PCT/TR2011/000095 dated Aug. 4, 2011 (9 pages).
International Search Report and Written Opinion for International Application No. PCT/TR2011/000210 dated Mar. 7, 2012 (7 pages).

* cited by examiner

DRY POWDER INHALER

CROSS-REFERENCE TO RELATED APPLICATIONS

This application is a division of U.S. application Ser. No. 13/451,838, filed Apr. 20, 2012, now U.S. Pat. No. 9,345,848, which is a continuation-in-part of PCT Application No. PCT/TR2010/000210, filed Oct. 20, 2010, and PCT Application Nos. PCT/TR2011/000085, PCT/TR2011/000086, PCT/TR2011/000087, PCT/TR2011/000088, PCT/TR2011/000089, PCT/TR2011/000090, PCT/TR2011/000091, PCT/TR2011/000093, PCT/TR2011/000094, and PCT/TR2011/000095, filed Apr. 13, 2011, each of which is incorporated herein by reference in its entirety. U.S. application Ser. No. 13/451,838 also claims priority to Turkish Patent Applications TR2009/07917, filed Oct. 20, 2009, TR2010/02877, filed Apr. 13, 2010, TR2010/03091, filed Apr. 20, 2010, TR2010/03238, filed Apr. 26, 2010, TR2010/04307, TR2010/04308, TR2010/04310, TR2010/04312, TR2010/04313, and TR2010/04317, filed May 28, 2010.

BACKGROUND OF THE INVENTION

It is rather common to use inhalers for delivering medicaments utilized in the treatment and prophylaxis of respiratory diseases. Inhalation treatment is the most commonly preferred treatment method in these diseases as the inhalers provide ease of use; the medicaments have rapider onset of time resulting from local administration and they have fewer side effects. Various inhalers have been designed in order to provide effective and sufficient delivery of the medicaments used in the treatment of respiratory diseases, particularly in asthma and chronic obstructive pulmonary disease. These inhalers vary according to their operating mechanisms and the physical form of the medicament to be delivered.

In the inhalers used to deliver the medicaments in dry powder form, the medicament is carried in reservoirs, capsules or blisters packages. It is highly significant to deliver each dose to the patient with exact accuracy and preciseness since the required medicament dose in the inhalation is very low.

In general, one blister pocket containing medicament in dry powder form is opened in response to each actuation of the device in inhalers comprising blister packages. One blister pocket containing one dose of dry powder medicament is usually opened by peeling the blister package indexed upon the actuation of the device or piercing the blister pocket by the piercing means in the inhaler. The inhalers comprising peelable blister packs enable the sufficient amount of the dry powder medicament contained in the opened blister to be easily inhaled as the airflow enters the opened blister pocket more easily in the inhalers comprising peelable blister packs than the inhalers comprising pierceable blister packs. Therefore, the blister package should be indexed enough to enable the blister pocket to be opened completely so as to realize an effective inhalation in response to each actuation of the inhaler. However, it is quite difficult to enable the blister package to be indexed properly to the same extent in each actuation of the device so as to realize a safe inhalation in the inhaler comprising peelable blister packages. In the case that the blister package that is indexed upon the actuation of the device is indexed less than the required extent, the blister pocket may not be opened completely while more than one blister pocket may be opened in the case that the blister package is indexed more than the required extent. The fact that one blister pocket cannot be opened completely and an effective inhalation cannot be realized as the sufficient amount of the active agent comprised in the dry powder medicament cannot be delivered to the patient or more than the required amount of the active agent is delivered to the patient as one blister pockets are opened lead to dangerous consequences. Therefore, controlled dosing of the medicament in dry powder form cannot be achieved when the blister package is not indexed properly to the same extent in response to each actuation of the inhaler.

The inhalation device marketed under the trade mark Diskus® by GlaxoSmithKline is one of the most well-known inhalers on the market. This device operates with a slide mechanism and a blister strip package in which the dry powder medicament is carried. However, this device needs to be improved in terms of specifications to enable the blister package to be properly indexed to the same extent in response to each actuation of the device.

The inventor has surprisingly found that the force of attraction imposed by the winding wheel on the lid sheet is balanced, and thus the blister package is properly indexed to the same extent in response to each actuation of the device in the case that each of the preferably polyoxymethylene resilient wings of the winding wheel, on which the lid sheet of the blister package peeled upon the actuation of the inhaler is coiled, is composed of three parts in the inhaler comprising peelable blister package.

To this respect, the present invention relates to an inhaler comprising peelable blister package appropriate for delivering dry powder medicament which enables the blister package to be indexed properly to the same extent in response to each actuation of the inhaler.

DETAILED DESCRIPTION OF THE INVENTION

The inhaler pertaining to the present invention is an easy-grip, manual device which is suitable to be used for the delivery of the medicament in dry powder form.

The housing of the device pertaining to the present invention has been designed such that each component of the blister package and the gear mechanism which have a significant role in enabling the device to work properly is situated accurately and works harmoniously. To this end, the housing is divided into several compartments. The used portion and the unused portion of the blister package are accommodated in separated compartments in order to prevent the residual dry powder medicament in the opened blister pocket spilling on the other components of the housing. Furthermore, the housing also comprises a beak which enables the blister package to be peeled and a manifold through which the dry powder medicament in the open blister pocket passes before reaching the mouthpiece during the inhalation. The housing can be in any appropriate shape through it is preferably elliptic or circular.

Figure 1A:
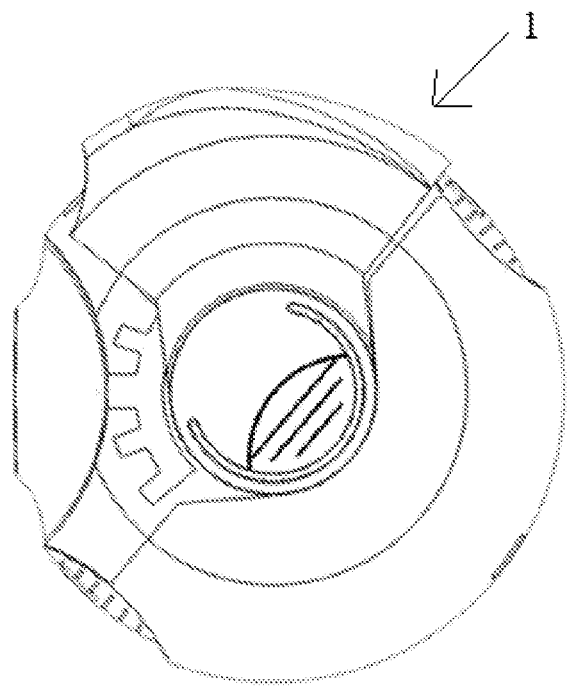
FIG. 1a is a perspective view of the inhaler according to the present invention.
Figure 1B:
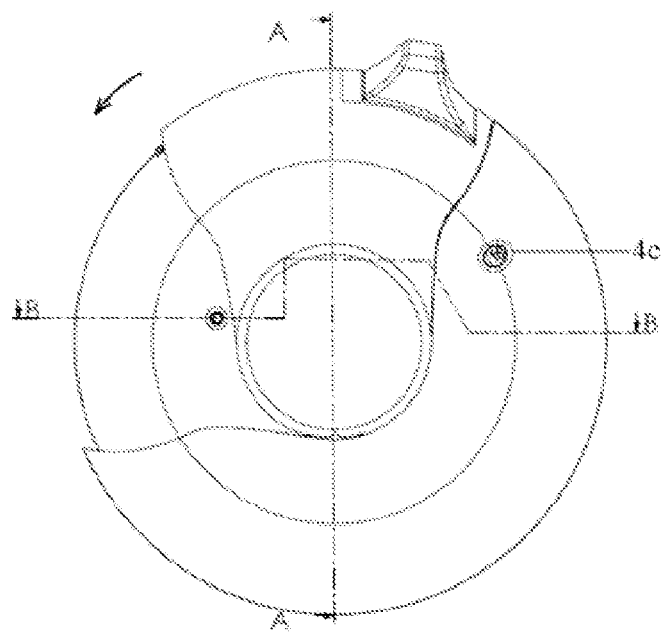
FIG. 1b is another perspective view of the inhaler according to the present invention.
Figure 1C:
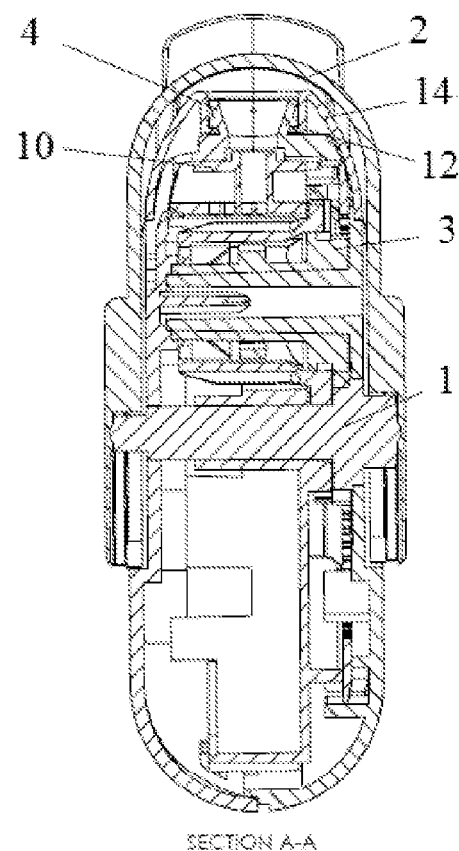
FIGS. 1c and 1d are views of the A-A and B-B cross sections of the inhaler of the present invention, respectively.
Figure 1D:
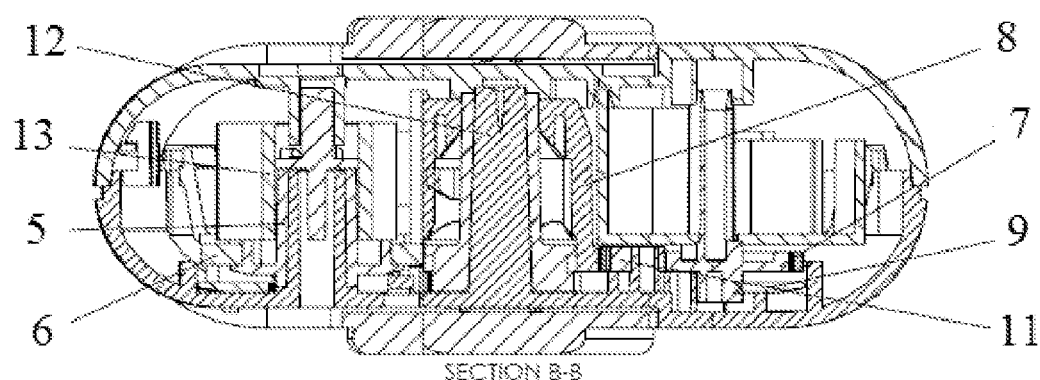
Figure 2A:
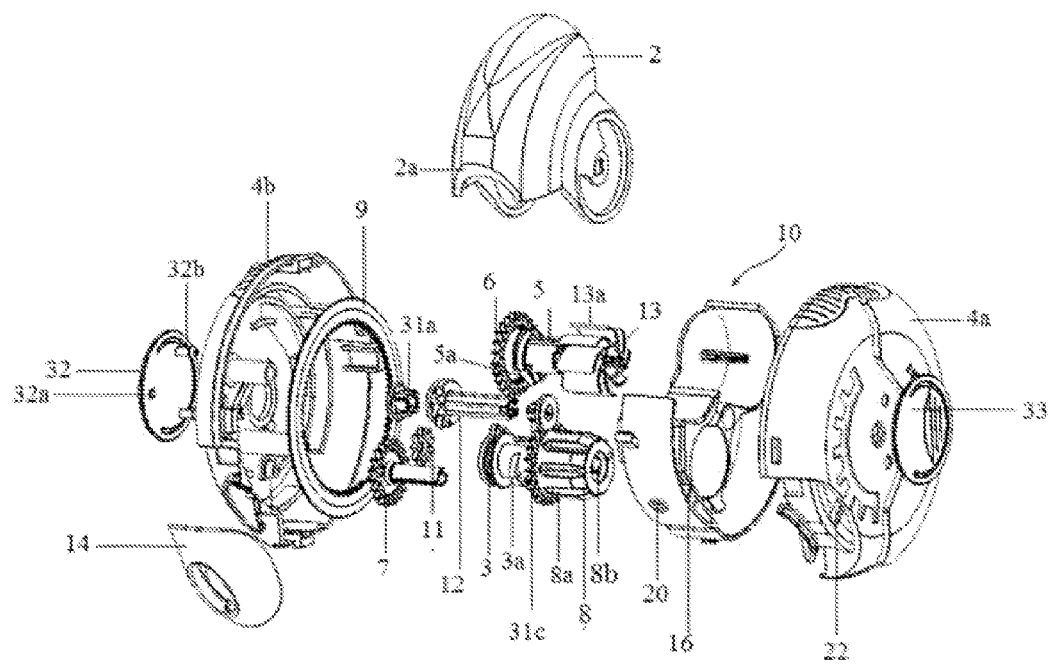
FIG. 2a is an exploded view of the inhaler according to the invention.
Figure 2B:
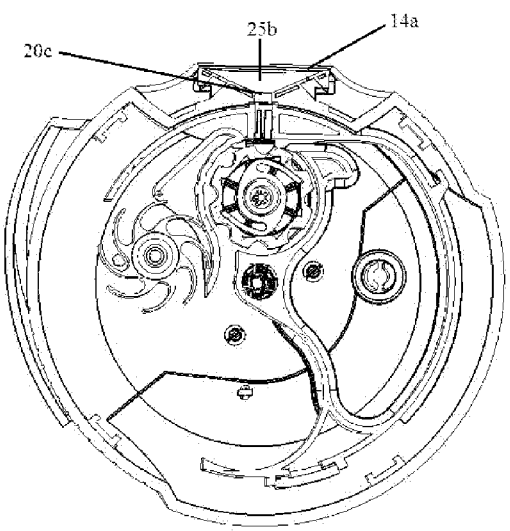
FIG. 2b is a vertical cross-sectional view of the inhaler according to the present invention.

The inhaler (1) pertaining to the present invention comprises a gear mechanism situated in the housing (10) between the upper housing member (4*a*) and the lower housing member (4*b*) in order to enable the inhalation of the dry powder medicament carried in a blister package (15) as displayed in FIGS. 1*a* and 2*a*. Each component of the inhaler (1) is positioned at suitable spots on the housing (10) to guarantee their working properly and accurately. The cross-sectional view A-A in FIG. 1*c* and the cross-sectional view B-B of FIG. 1*d* clearly display the communication of the gear mechanism with the other components of the inhaler (1) and their locations.

The inhaler (1) pertaining to the present invention shown in FIGS. 1*a* and 2*a* is ready for inhalation. In this case, the mouthpiece cover (2) is in the second position and the mouthpiece (14) is entirely exposed. The mouthpiece cover (2) has to be rotated by holding on the carved part (2*a*) on one end of the mouthpiece cover (2) in order to switch to the second position from the first position wherein the mouthpiece is completely covered. In this way, the mouthpiece (14) is completely exposed when the mouthpiece cover (2) is switched to the second position from the first position and the gear mechanism is triggered by the drive gear (12). The drive gear (12) precisely transmits the movement of the mouthpiece cover (2) to the indexing ratchet wheel (3).

Figure 3:
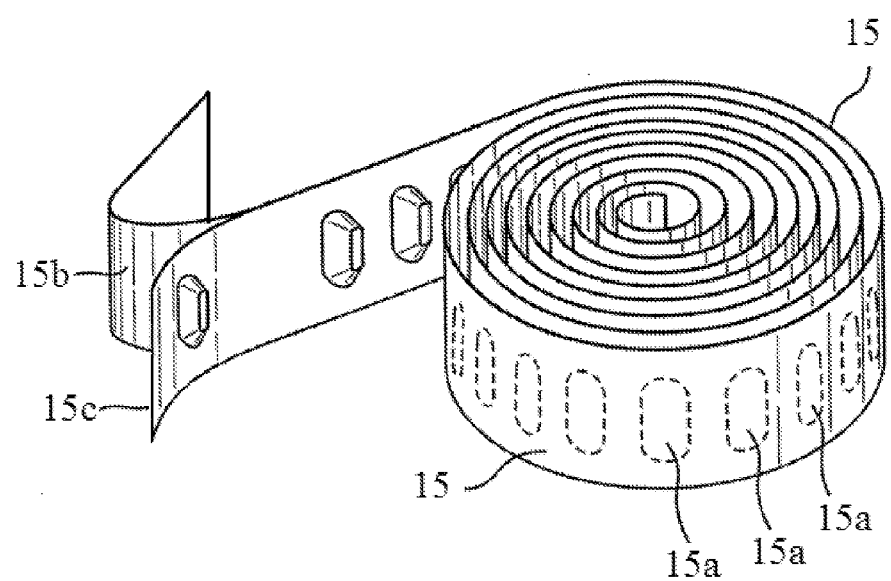
FIG. 3 is a perspective view of the blister pack for use with the inhaler according to the invention.

The indexing wheel (8) which engages with the indexing ratchet wheel (3) enables the blister package (15) shown in FIG. 3 to be indexed. The blister pockets (15*a*) composing the blister package are received in the recesses (8*a*) on the indexing wheel and the blister package (15) is indexed when the indexing wheel (8) rotates. In the inhaler pertaining to the present invention, shapes of the recesses (8*a*) on the indexing wheel (8) have been designed to match the shapes of the blister pockets (15*a*) composing the blister package (15) for the blister package to be indexed properly.

The movement of the indexing wheel (8) is transmitted to the base gear (7) engaging with the pinion gear (11) by the pinion gear (11). The small gear which is under the base gear (7) and attached to it engages with the counter gear (9). Thus, the movement of the indexing wheel (8) is transmitted to the counter gear (9) shown in FIG. 13 by the pinion gear (11) and the base gear. There are numerals incrementing from 1 to 60 in the counter gear (9) displayed in FIG. 13. The angles between these numerals are all equal and approximately 5 degrees. The movement of the indexing wheel (8) by 45 degrees in response to each actuation of the device causes the counter gear to move approximately 5 degrees and the number of the unused blister pockets remained in the device to be clearly seen through the display aperture (4c) on the lower housing member (4b).

The blister package (15) shown in FIG. 3 is composed of the lid sheet (15b) which provides impermeability and the base sheet (15c) on which the blister pockets (15a) are spaced at equal intervals. Each blister pocket contains medicament in dry powder form comprising one or more active agents.

The rotational movement that the mouthpiece cover (2) of the device executes while switching from the first position to the second is transmitted to the indexing ratchet wheel (3) via the drive gear (12) that the mouthpiece cover (2) engages with. As displayed in FIG. 2a, arms (3a) of the indexing ratchet wheel interlocks with protrusions inside the indexing wheel (8) and rotates the indexing wheel (8) unidirectionally. Therefore, the blister package (15) is indexed forward while the indexing wheel (8) rotates as the blister pockets (15a) composing the blister package (15) are received in the recesses (8a) of the indexing wheel. The beak (16) in the housing (10) provides the blister package (15) to be peeled while the blister package (15) is indexed and provides one blister pocket (15a) to be opened in response to each actuation of the inhaler (1).

The winding wheel gear (6), which is another component of the gear mechanism, engages with the indexing wheel (8) as displayed in FIG. 2a. The mechanism gear (5) that interlocks with the winding wheel (13) from inside has arms (5a) to interlock with the interior teeth of the winding wheel gear (6). When the indexing wheel (8) rotates the winding wheel gear (6), the winding wheel rotates unidirectionally owing to the arms of the mechanism gear (5a) which interlocks with the interior teeth of the winding wheel gear (6) and the lid sheet (15b) which is peeled away while the blister package is indexed is tightly coiled on the resilient wings (13a) of the winding wheel. The base sheet (15c) of the blister package (15) where the blister pockets are spaced is accumulated in a separate part (18a) of the device (FIG. 4j). Each resilient wing (13a) of the winding wheel extends from the center of the winding wheel (13) to the end.

Figure 12:
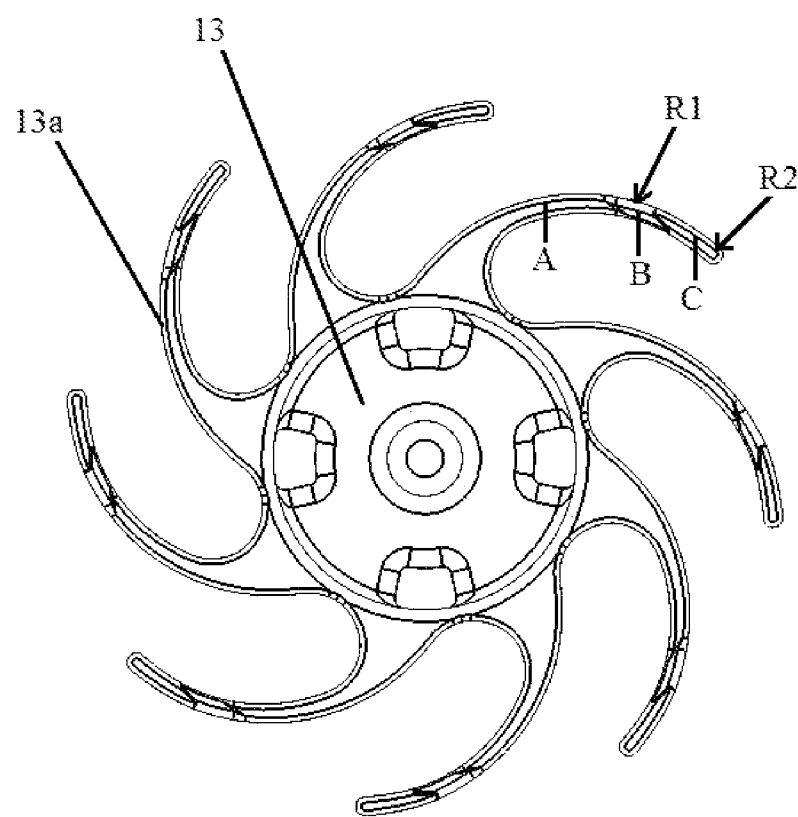
FIG. 12 is a perspective view of the winding wheel pertaining to the present invention.

As illustrated in FIG. 12, the winding wheel (13) of the inhaler pertaining to the present invention is composed of a plurality of resilient wings which are preferably made of polyoxymethylene plastics. Each of these resilient wings (13a) is composed of three parts (A, B, C) each of which has different radius values. Thus, these resilient wings (13a) stretch enough to balance the force of attraction imposed on the lid sheet (15b) of the blister package, therefore on the blister package (15), as the thickness of the lid sheet (15b) of the blister package coiling on them increases, and they enable the blister package (15) to be indexed properly to the same extent in response to each actuation of the inhaler. The resilient wings of the winding wheel illustrated in FIG. 12 are composed of 3 parts (A; B; C). The average radius (R1) of the second part (B) of each resilient wing is in the range of 4.60 mm to 5.20 mm, preferably in the range of 4.75 mm to 5.15 mm; and the radius (R2) of the piece of the third part (C) that curls through the end of the resilient wing is in the range of 0.9 mm to 1.70 mm, preferably in the range of 1.10 mm to 1.50 mm.

Figure 4A:
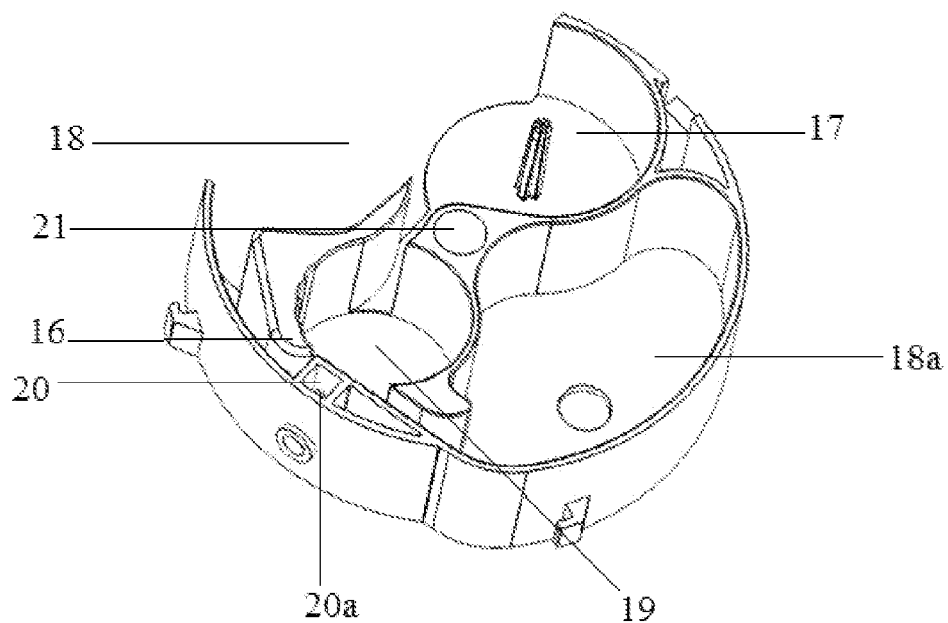
FIGS. 4a and 4b are perspective views of the housing of the inhaler according to the invention.
Figure 4B:
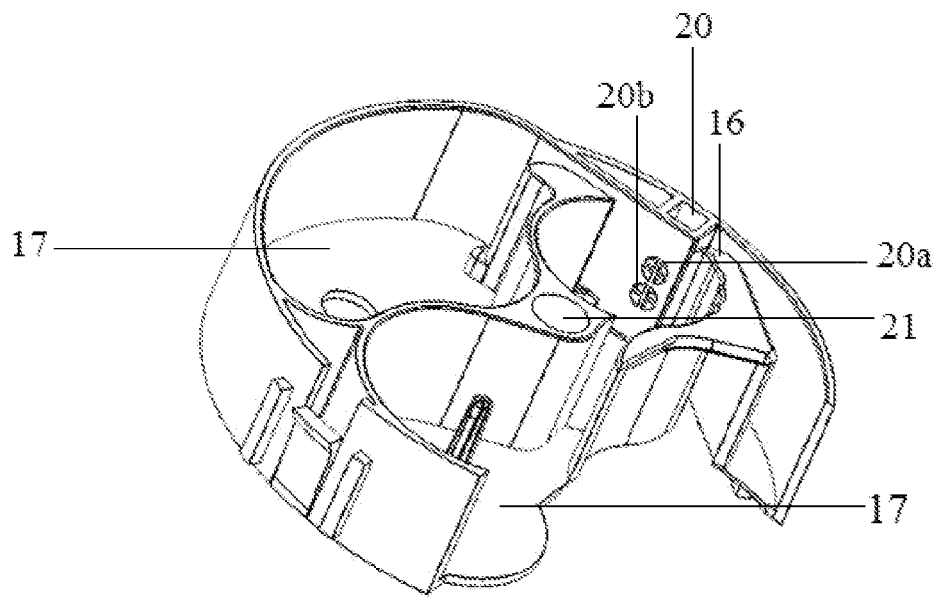

Different views of the housing (10) wherein the gear mechanism and the other components of the inhaler (1) pertaining to the present invention are arranged are displayed in FIGS. 4a and 4b. Furthermore, as can be seen in FIGS. 4a through 4j, the housing (10) also comprises the components having significant roles in the actuation of the device such as the beak (16), the manifold (20), the apertures with four sub-apertures (20a, 20b). Each component comprised in the housing is situated in appropriate parts of the housing (10) in order to enable the inhaler (1) to work properly. The drive gear (12) passes through the center (21) of the housing and joins the mouthpiece cover (2) at both sides of the inhaler. The blister package (15) is in the lower part (17) of the housing as coiled up. In response to each actuation of the inhaler (1), the blister package (15) is peeled by the beak (16) in the housing while being indexed by the indexing wheel (8) situated in the upper part (19) of the housing. The lid sheet (15b) of the blister package (15) which provides impermeability is indexed over the beak (16) and coiled on the winding wheel (13) which is situated in the side part (18) of the housing. The base sheet (15c) of the blister package (15) on which the blister pockets (15a) are spaced, on the other hand, is accumulated in the separated compartment (18a) of the housing (10). Upon the inhalation of the patient, the air passes through the air inlet with four sub-apertures (20a) under the manifold (20) into the opened blister pocket; entrains the dry powder medicament contained in the opened blister pocket (15a) in response to each actuation of the device; provides it to pass through the other aperture with four-sub-apertures (20b) and reach the mouthpiece via the manifold (20).

The housing (10) and the other components of the inhaler (1) pertaining to the present invention are stably kept together as the upper housing member (4a) and the lower housing member (4b) displayed in FIGS. 5a through 5h are joined together. The engagement tabs (28) on the inside surface of the lower housing member (4b) engage with the engagement recesses (27) on the inside surface of the upper housing member (4a) and the upper and lower housing members are fixed tightly. Therefore, the protrusions (23a, 23b) on the upper housing member (4a) and the protrusions (24a, 24b) on the lower housing member (4b) are joined end to end and they define the restricted path for the rotational movement of the mouthpiece cover (2). The mouthpiece cover (2) can be moved along this path. When the mouthpiece cover (2) is on the first position, the mouthpiece is completely covered, the device is in standby mode and the mouthpiece cover (2) leans on the first protrusion (23a) on the upper housing member and the first protrusion (24a) on the lower housing member. The mouthpiece (14) is manually slid along the rotational path with the help of the carved part to switch to the second position. The mouthpiece is completely exposed when the cover is in this position, one dose of the dry powder medicament is ready for inhalation and the mouthpiece cover (2) leans on the second protrusion (23b) on the upper housing member and the second protrusion (24b) on the lower housing member.

Figure 4C:
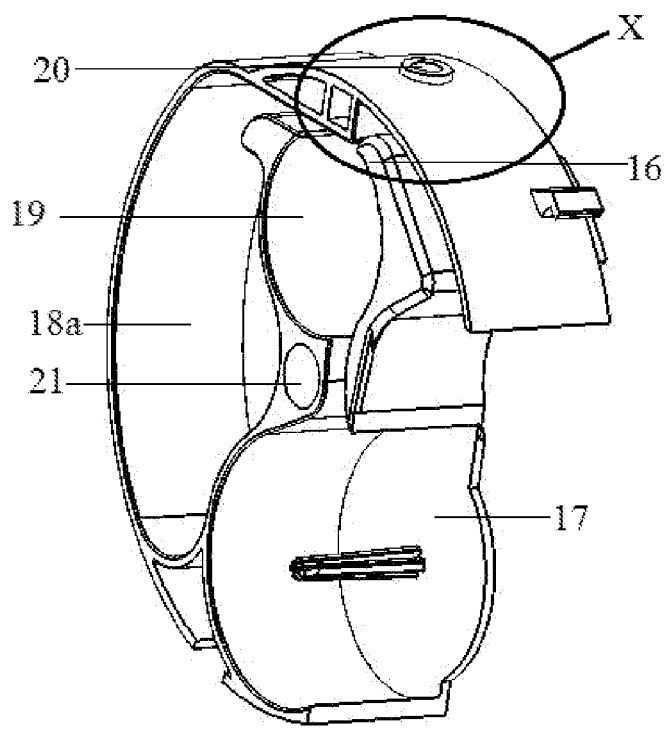
FIG. 4c is another perspective view of the housing of the inhaler according to the invention.
Figure 4D:
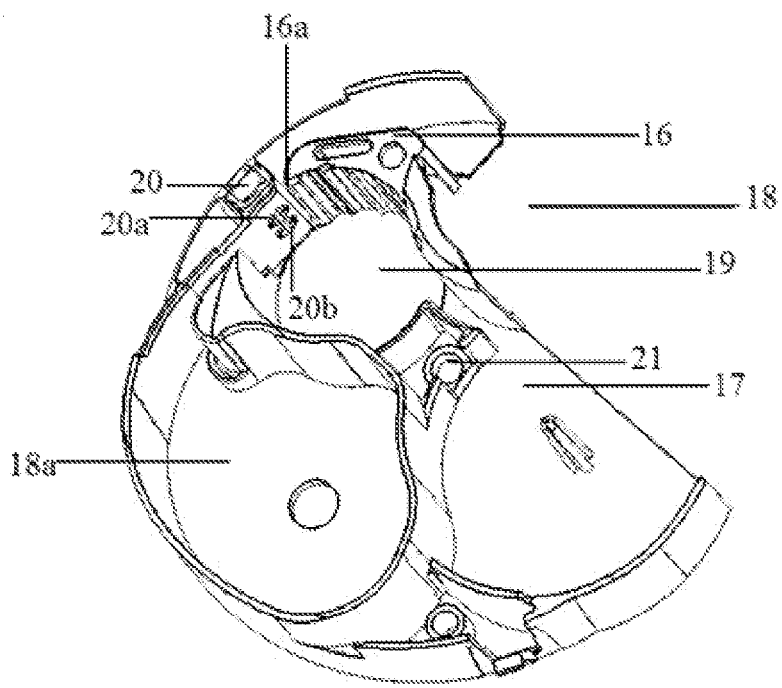
FIG. 4d is another perspective view of the housing of the inhaler of the invention.
Figure 4E:
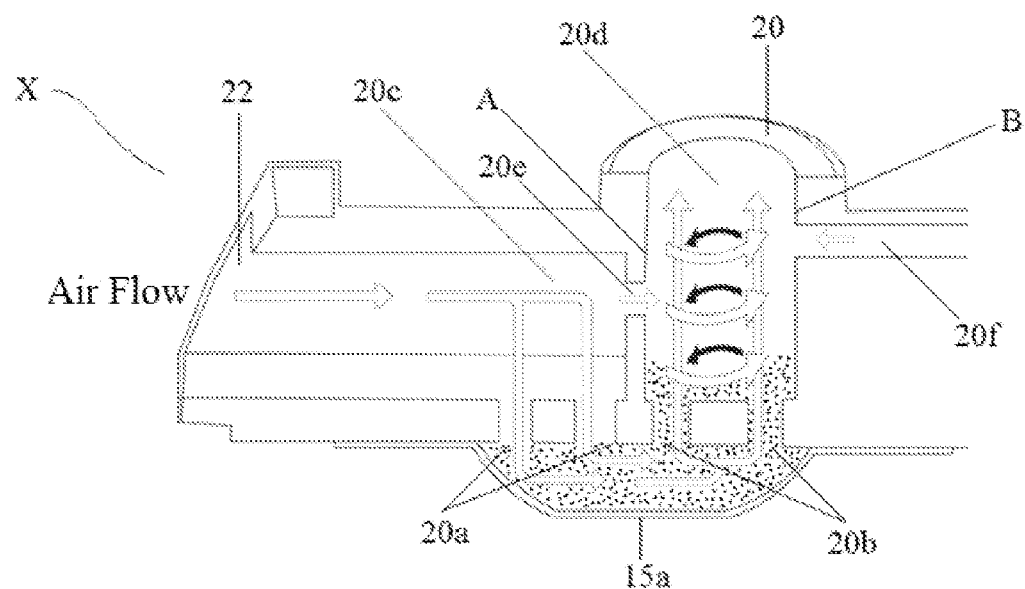
FIGS. 4e and 4f are cross-sectional views of the manifold part of the inhaler pertaining to the invention which is shown as X in FIG. 4c.
Figure 4F:
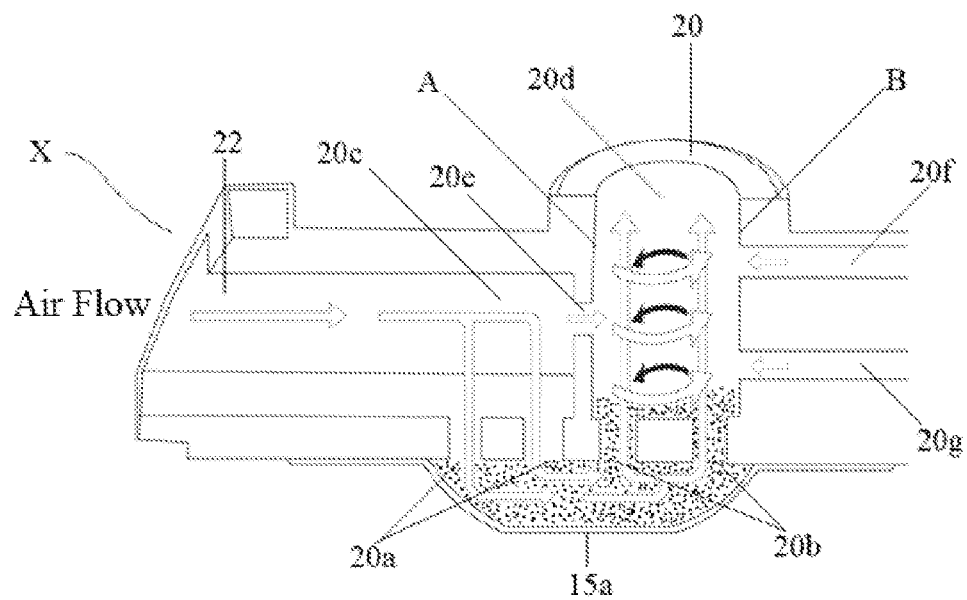
Figure 4G:
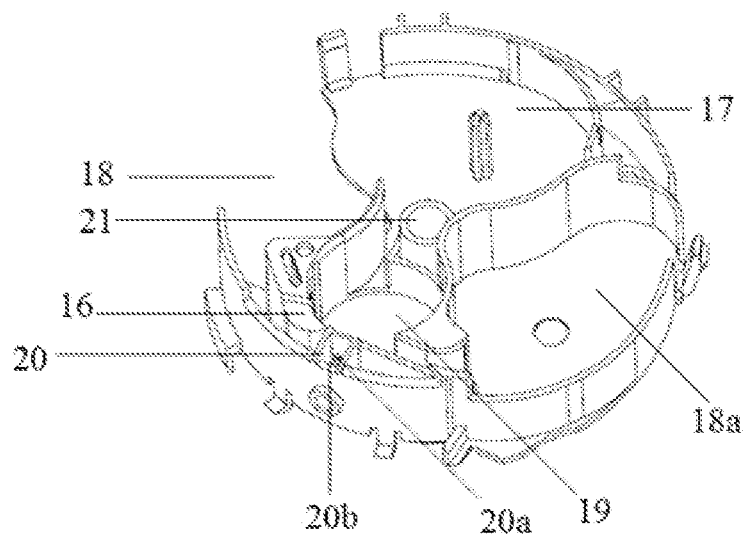
FIGS. 4g and 4h are perspective plan and bottom views of the housing of the inhaler according to the invention, respectively.
Figure 4H:
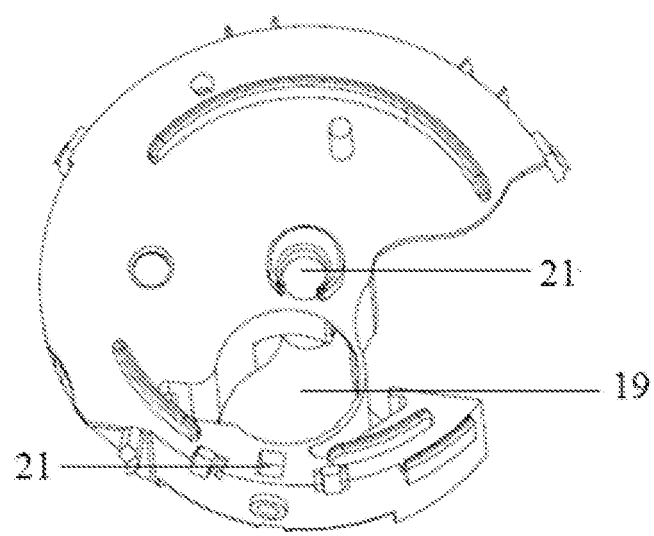

A view of the cross-section of the housing (10) which illustrated as X in FIG. 4c and includes the manifold (20) is given in FIGS. 4e and 4f. According to FIG. 4e, the blister pocket (15a) opened upon the actuation of the inhaler (1) is positioned immediately under the apertures with four sub-apertures (20a, 20b). There are two apertures with four sub-apertures (20a, 20b) on the edge of the manifold (20) which is close to the blister (15a) and they are partitioned off from each other by a wall. This wall is named as wall A in FIG. 4c and it partitions the manifold (20) into two parts. Wall A lies between the first part (20c) and the second part (20d) of the manifold and it belongs to both the first part (20c) and the second part (20d) of the manifold. Upon the respiration of the patient so as to inhale the medicament in dry powder form in the opened blister pocket (15a), the external air that enters the inhaler passing through the air inlet (22) on the upper housing member reaches the first part (20c) of the manifold. Some part of this airflow reaches the opened blister (15a) by passing through the aperture with four sub-apertures (20a) on the edge of the first part of the manifold. The airflow reaching the opened blister pocket (15a) entrains the dry powder medicament in the blister to the second part (20d) of the manifold through the other aperture with four sub-apertures (20b) on the edge of the manifold which is close to the blister. Wall A and wall B shown in FIG. 4c are two opposite walls in the second part (20d) of the manifold. Some part of the external air which runs through the air inlet (22) and enters the inhaler (1) upon the patient's breathing in passes through the first part (20c) of the manifold and reaches the opened blister pocket (15a) while the rest passes through the aperture (20e) on wall A and the aperture (200 on wall B and enters the second part (20d) of the manifold. The apertures (20, 200 on wall A and wall B are asymmetrically positioned. Shapes and the cross-sections of the apertures (20e, 200 on wall A and wall B can be identical or different. Thus, an effective turbulence is created in the second part (20d) of the manifold as the speed of the airflow entering through the aperture (20e) on wall A and the speed of the airflow entering through the aperture (200 on wall B are different. The created turbulence disperse the agglomeration of the dry powder medicament entrained to the second part (20d) of the manifold and provides the dry powder medicament to be delivered to the patient at appropriate particle size distribution.

Another cross-sectional view of the part of the housing which is shown as X in FIG. 4c is given in FIG. 4f. In the cross-sectional view of the manifold illustrated in FIG. 4f, there are two apertures (20f, 20g) on wall B of the manifold differently from FIG. 4e. The apertures (20e, 200 on wall A and wall B are asymmetrically positioned with respect to each other. The shapes and the cross-sections of the apertures (20e, 20f, 200 on wall A and wall B which allow the air in the second part (20d) of the manifold can be identical or different. Thus, the airflow entering in through the aperture (20e) on wall A and the airflows entering in through the apertures (20f, 20g) on wall B create an effective turbulence in the second part (20d) of the manifold. This turbulence disperses the agglomeration in the dry powder medicament entrained to the second part (20d) of the manifold and enables the medicament in dry powder form to be delivered to the patient at an appropriate particle size distribution.

Figure 5A:
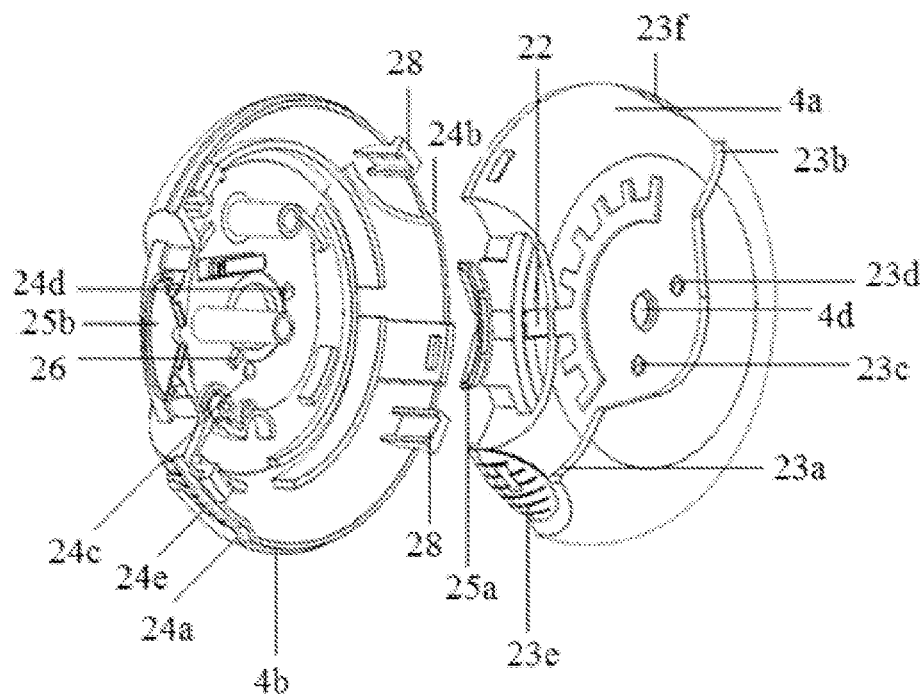
FIGS. 5*a* and 5*b* are perspective views of upper and lower housing members of the inhaler according to the invention, respectively.
Figure 5B:
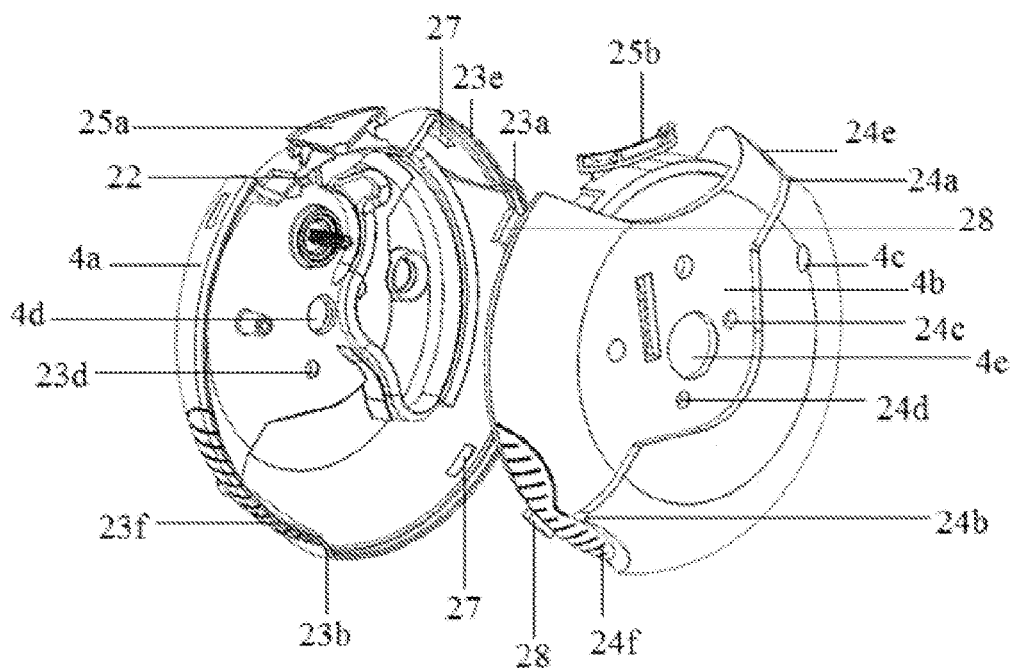
Figure 5C:
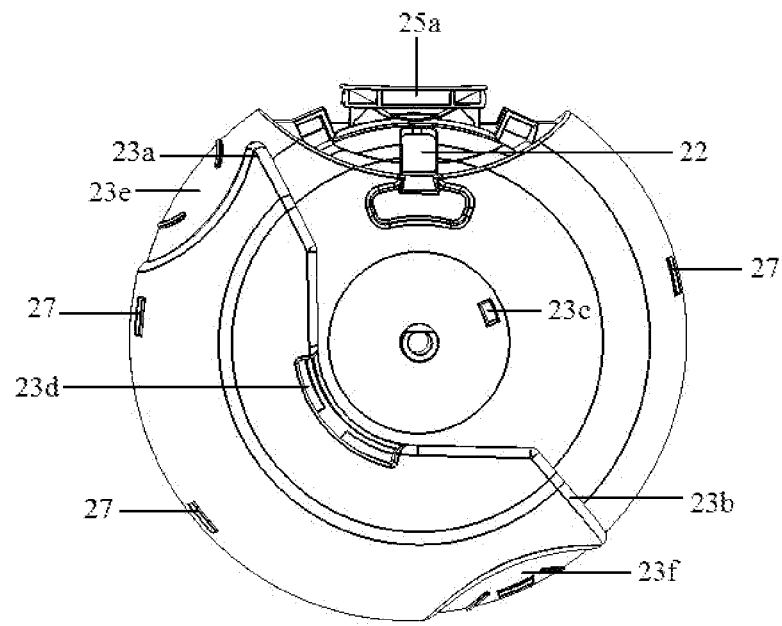
FIG. 5*c* is another perspective view of the upper housing member of the inhaler of the invention.
Figure 5D:
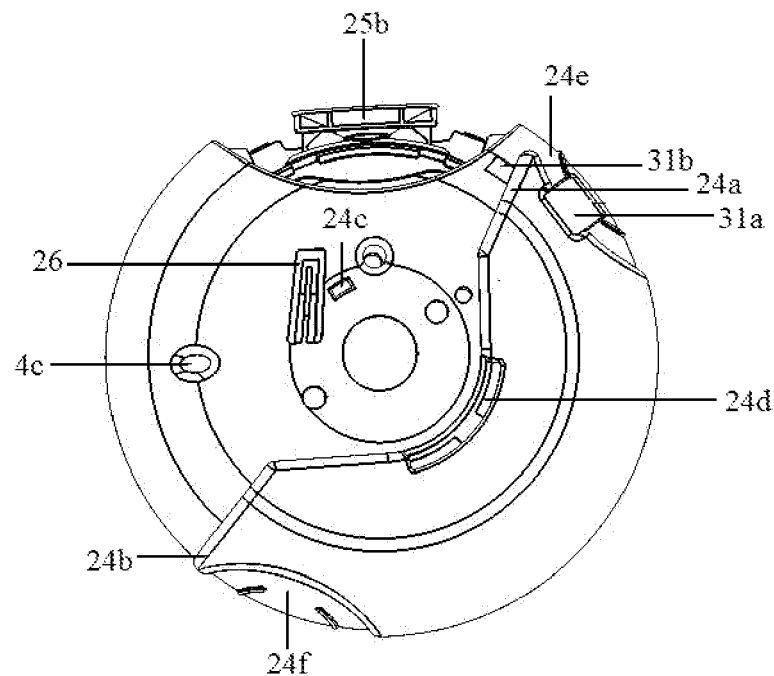
FIG. 5*d* is another perspective view of the lower housing member of the inhaler of the invention.
Figure 5E:
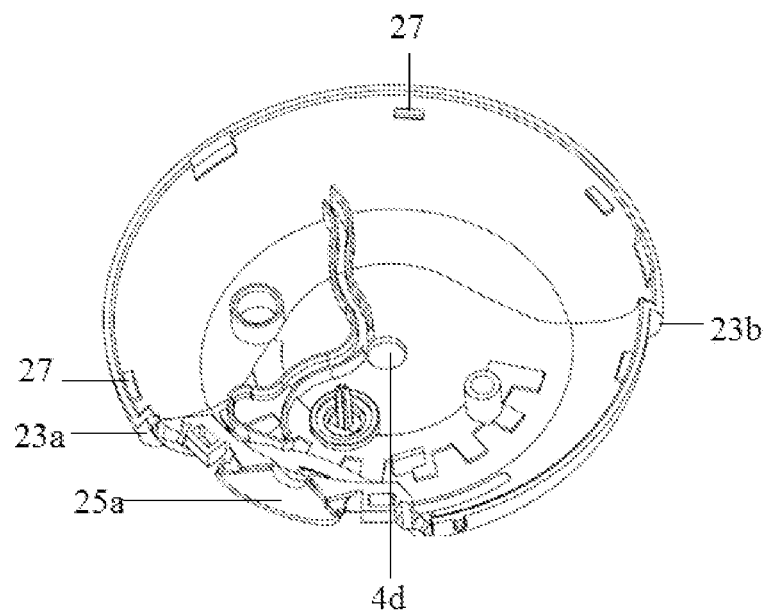
FIGS. 5*e* and 5*f* are perspective views of the inner and outer sides of the upper housing member of the inhaler according to the invention, respectively.
Figure 5F:
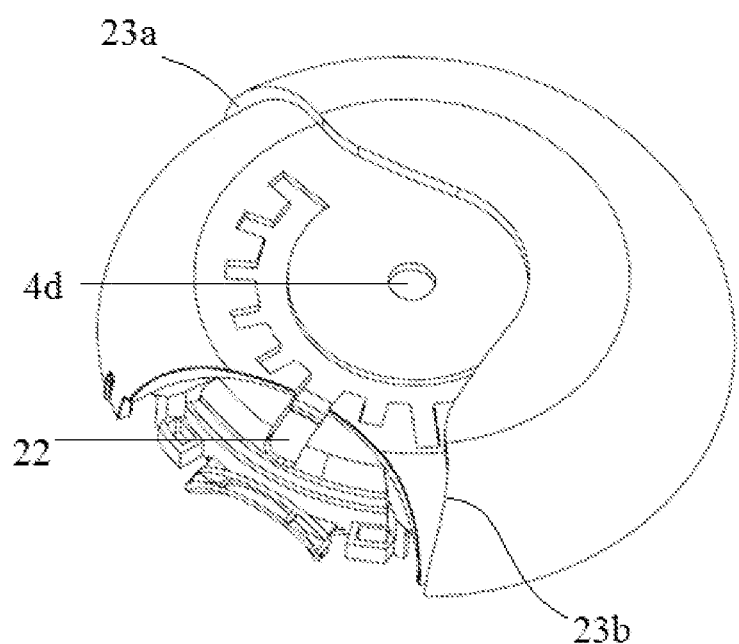
Figure 5G:
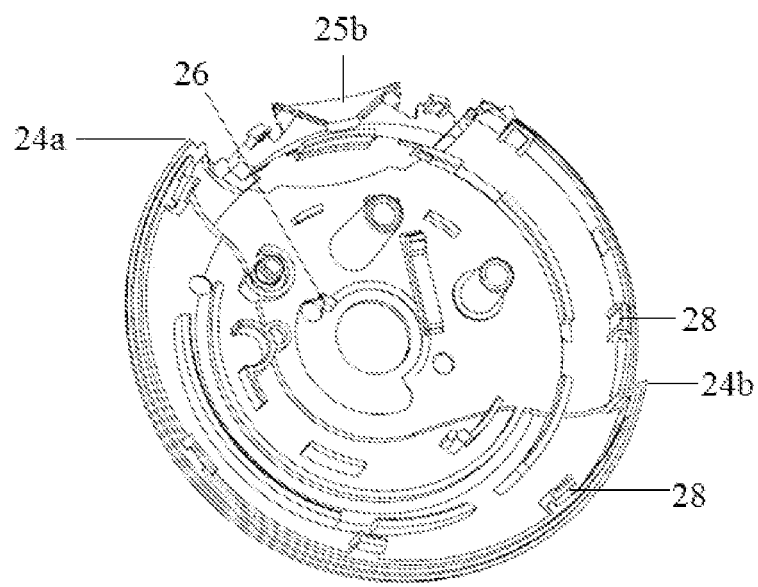
FIGS. 5*g* and 5*h* are perspective views of the inner and outer sides of the lower housing member of the inhaler according to the invention, respectively.
Figure 5H:
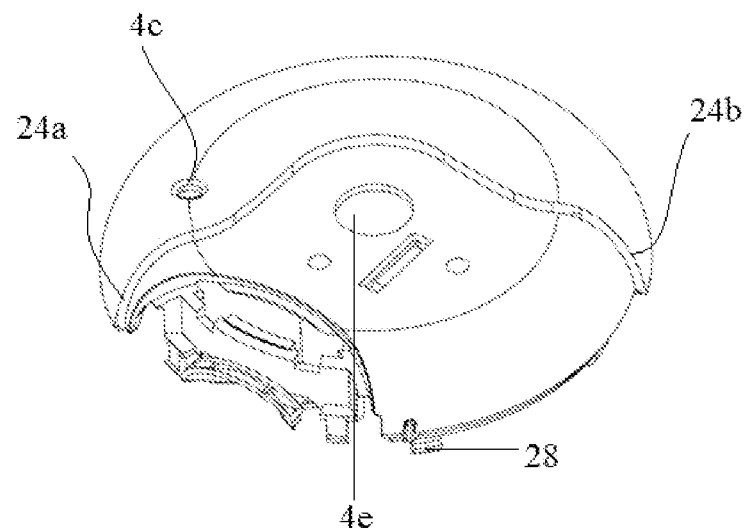
Figure 5I:
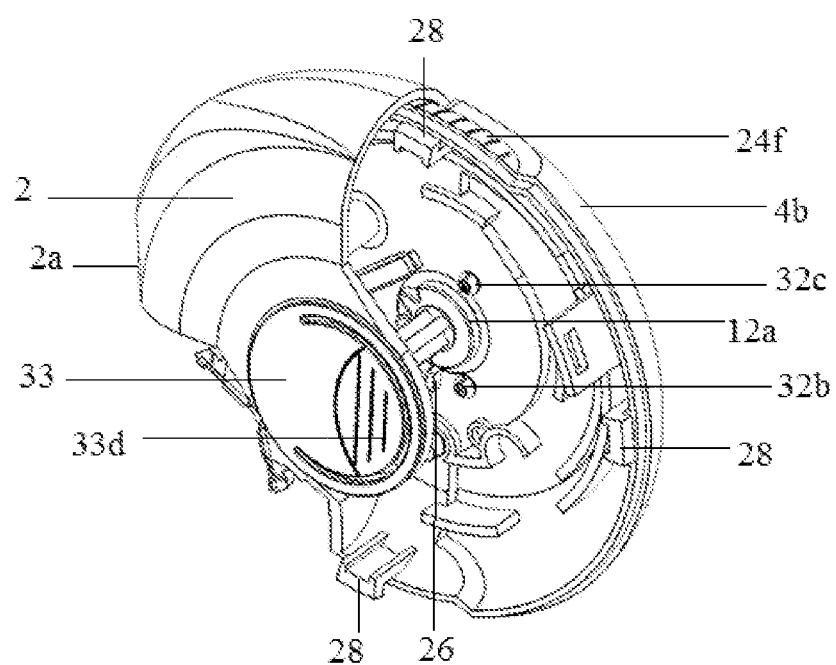
FIG. 5*i* is a cross-sectional view of the connection of the stabilizing resilient cover with the lower housing member in the inhaler pertaining to the invention.

The drive gear (12) passes through the aperture (4d) in the center of the upper housing member displayed in FIGS. 5e and 5f and the aperture (4e) in the center of the lower housing member, then it is joined with the mouthpiece cover (2) on two ends. There is a tapered channel between the manifold (20) and the mouthpiece (14). As displayed in FIGS. 5c and 5d, one half (25a) of the tapered channel that interconnects the manifold (20) that exist in the housing (10) with the mouthpiece (14) is comprised in the upper housing member (4a) while the other half of it (25b) is comprised in the lower housing member (4b). The channel is constituted as a whole when the upper (4a) and the lower (4b) housing members are joined together. Upon the inhalation of the patient, the air that enters the device through the air inlet (22) arranged in the upper housing member (4a) passes through the aperture with four sub-apertures (20a), reaches the opened blister (15a) and entrains the dry powder medicament there to the manifold (20) by passing it through the other aperture with four sub-apertures (20b). The grids on the upper housing member (23e, 230 and the grids on the lower housing member (24e, 240 prevent the slips of fingers when rotating the mouthpiece cover.

Figure 6A:
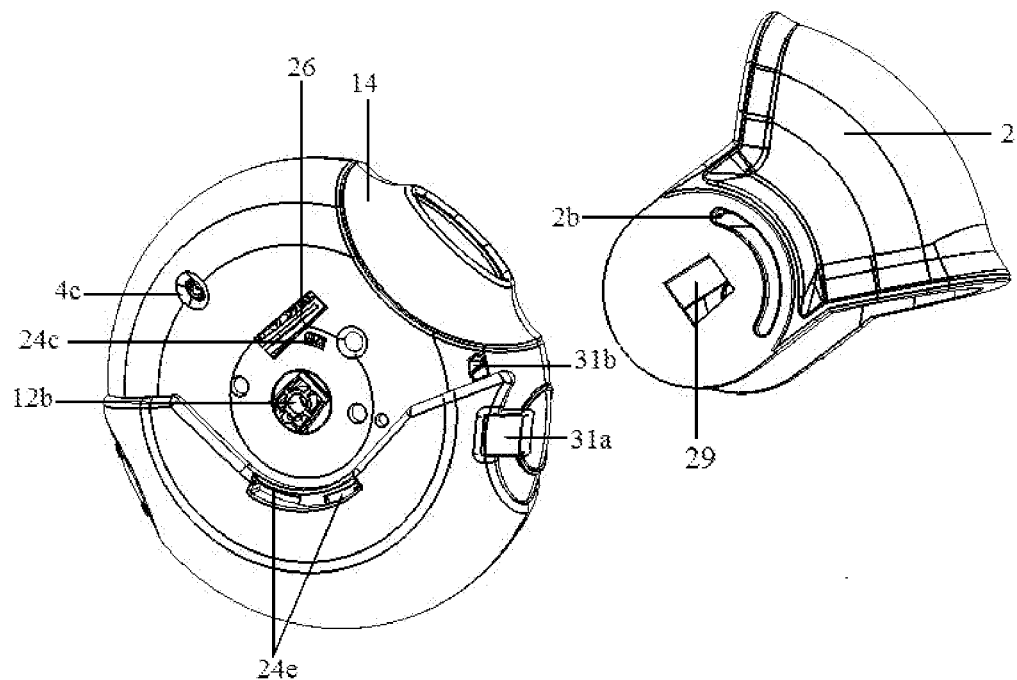
FIG. 6*a* is a view of the mouthpiece cover exploded from the inhaler.
Figure 6B:
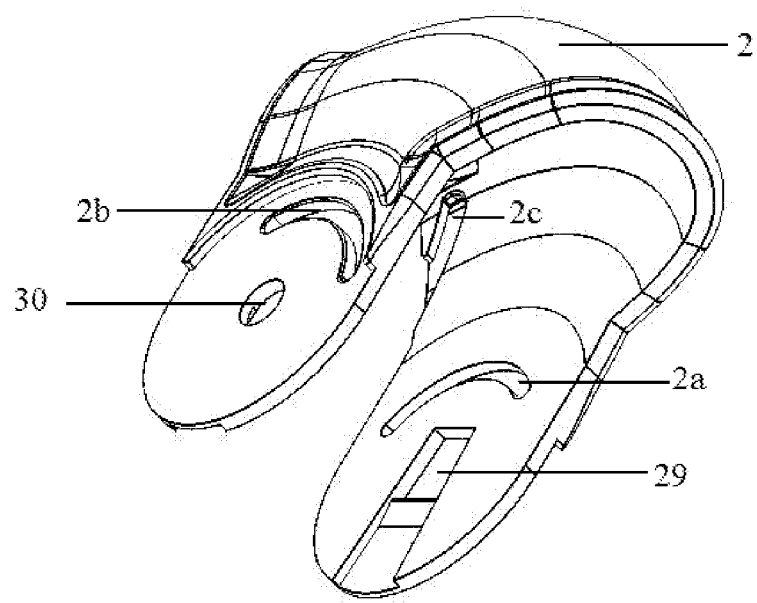
FIG. 6*b* is another perspective view of the mouthpiece cover of the inhaler of the invention.
Figure 6C:
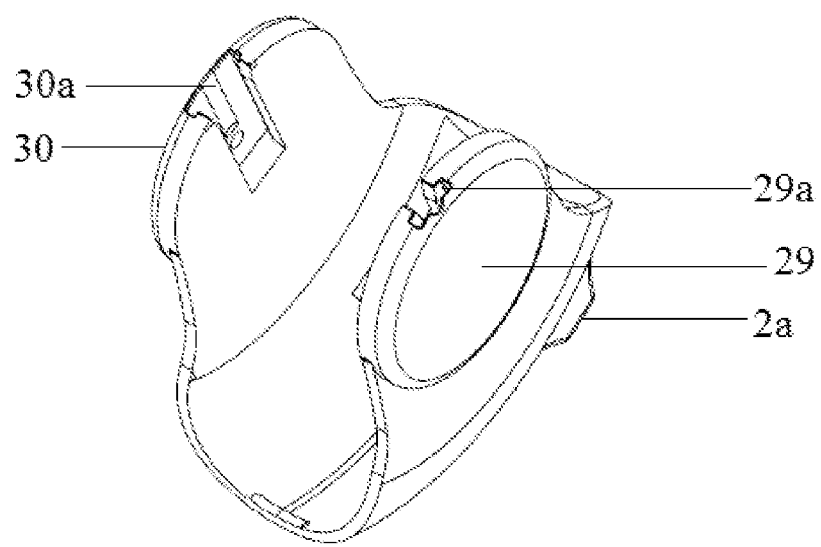
FIGS. 6*c* and 6*d* are perspective views of the inner and outer sides of the mouthpiece cover of the inhaler according to the invention, respectively.
Figure 6D:
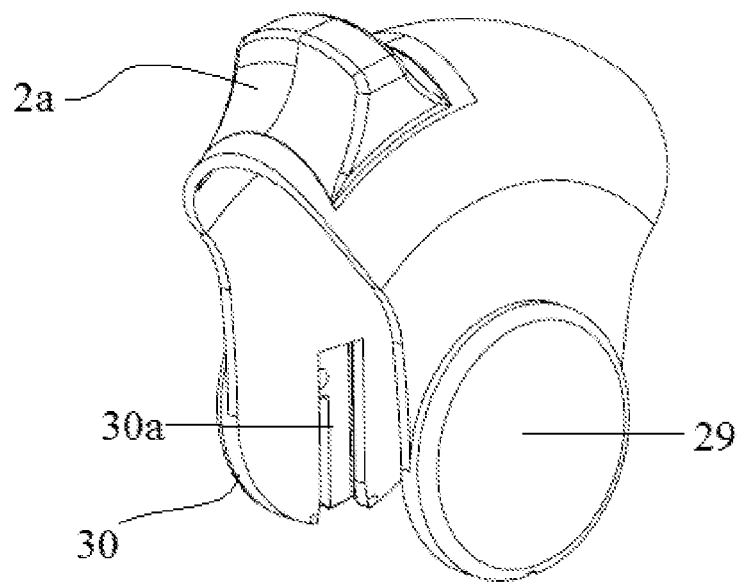
Figure 6E:
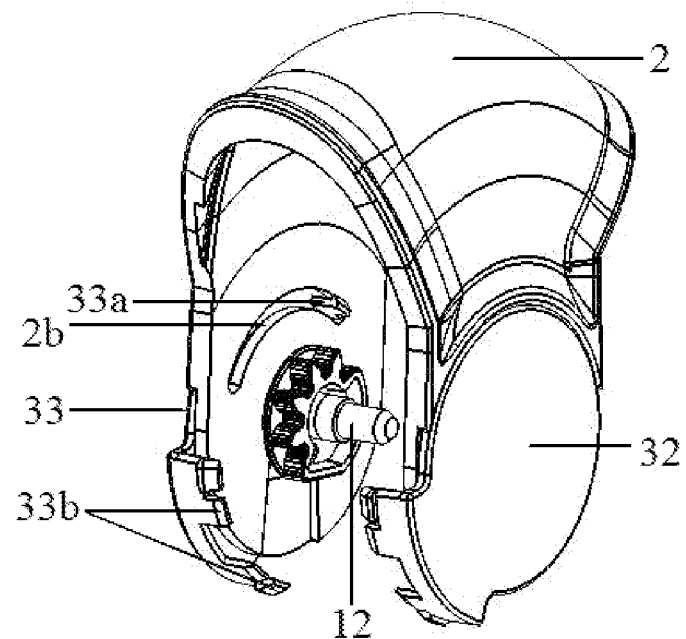
FIG. 6*e* is a perspective view of the connection between the mouthpiece cover, the drive gear, and the protective covers of the inhaler of the invention.
Figure 6F:
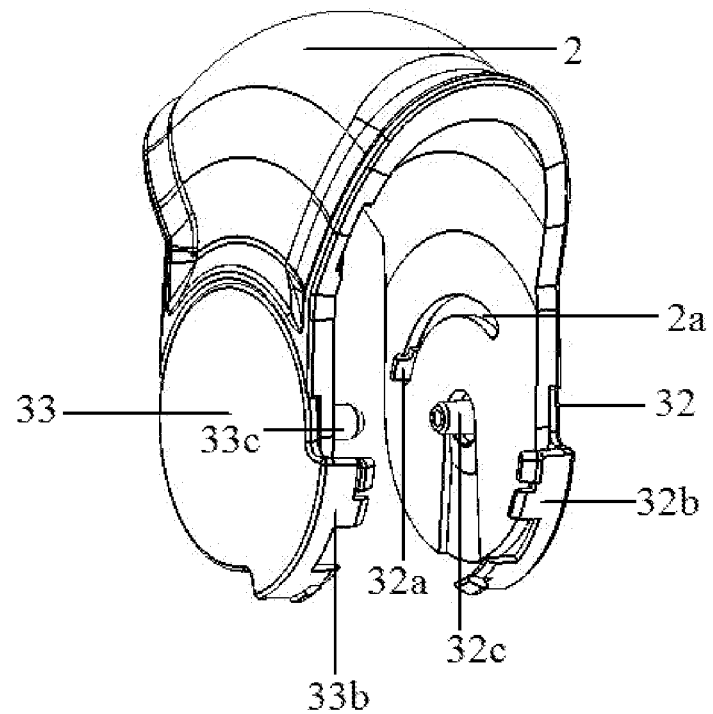
FIG. 6*f* is a perspective of the connection between the mouthpiece cover and the protective covers of the inhaler of the present invention.
Figure 6G:
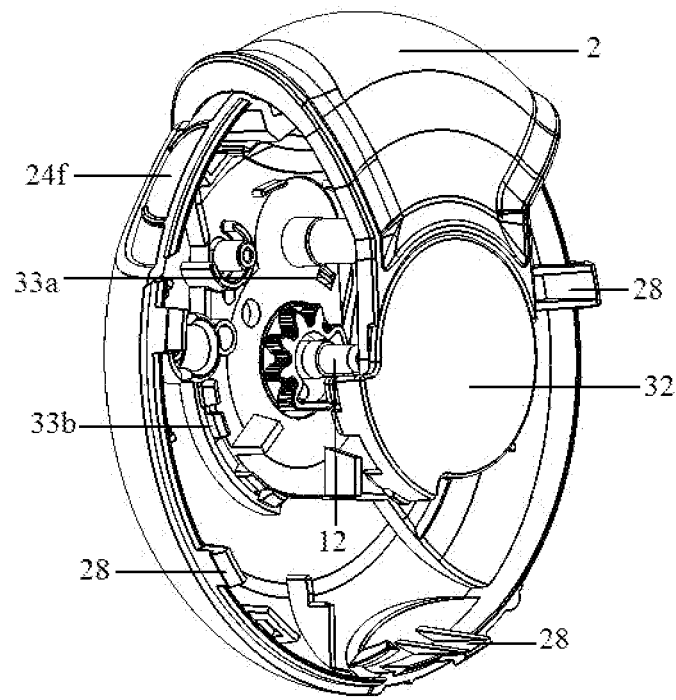
FIG. 6*g* is a perspective view of the connection between the mouthpiece cover, the drive gear, the lower housing member, and the protective cover of the inhaler of the present invention.
Figure 6H:
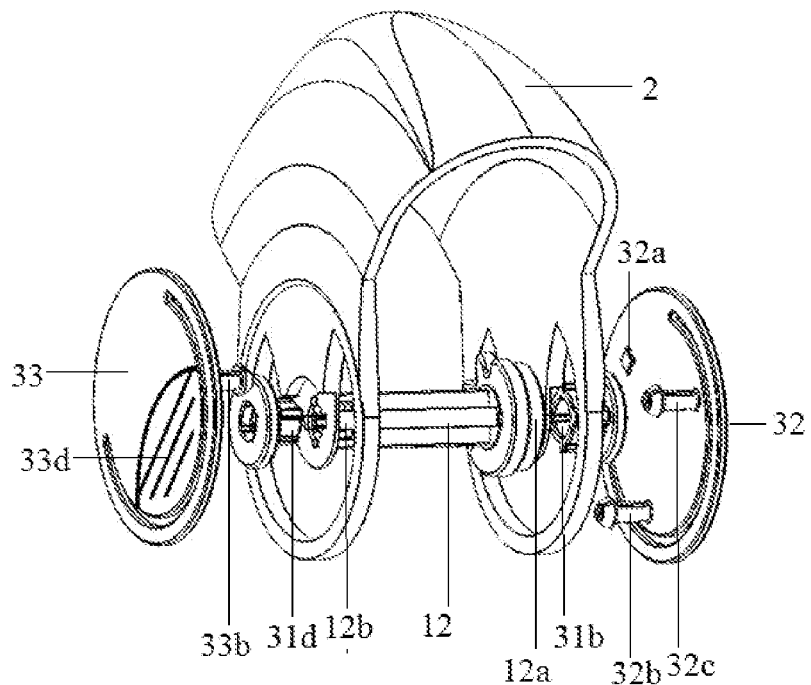
FIG. 6*h* is an exploded view of the communication between the mouthpiece cover, the drive gear and the stabilizing resilient covers in the inhaler according to the invention.

The mouthpiece cover (2) of the inhaler pertaining to the present invention is displayed in FIGS. 6a through 6f. The carved part, which is the finger tab (2a) in one end of the device enables the mouthpiece cover to be easily removed manually as seen in FIG. 6d. The finger tab (2a) has been designed to match the finger shape and is situated in any suitable spot on the mouthpiece cover (2). As can be seen clearly in FIGS. 6c and 6d, the first and the second connection points (29, 30) of the mouthpiece cover have recesses (29a, 30a) on their inside surfaces. Protrusions (31a, 31b) on the two ends of the drive gear (12) displayed in FIGS. 7e and 7f make a male-female connection with these recesses (29a, 30a). The first recess (30a) on the inside surface of the mouthpiece cover engages with the first protrusion (31a) on the one end of drive gear while the second recess on the inside surface of the mouthpiece cover (29a) engages with the second protrusion (31b) on the other end of the drive gear and the connection provided between each end of the drive gear (31a, 31b) and the corresponding recess (30a, 29a) on the inside surface of the mouthpiece cover is a male-female connection. The male-female connection that each end of the drive gear (31a, 31b) makes with the corresponding recessed parts on the inside surface of the mouthpiece cover (30a, 29a) causes to form an inside lock connection between the drive gear (12) and the mouthpiece cover (2) with maximum ±0.01% margin of error. Therefore, the rotational movement of the mouthpiece cover (2) on the upper (4a) and lower (4b) housing members is accurately transmitted to the indexing ratchet wheel by the drive gear (12) which has an inside lock connection with the mouthpiece cover (2) on its two ends.

The mouthpiece cover (2) is joined with the gear mechanism via the connection points. The drive gear consists of two ends (12a, 12b) and a hole (12c) at the center of one end as seen in FIG. 7g. Further, the drive gear (12) is joined with the connection points (29, 30) of the mouthpiece cover via the side covers (31a, 31c) as it can clearly be seen in FIGS. 6e, 6h, 6i and 6j illustrating the communication between the mouthpiece cover (2), the drive gear (12), side covers (31a, 31c) and the stabilizing resilient covers (32,33). Each of these side covers (31a, 31c) passes through the center (4d) of the upper housing member or the center (4e) of the lower housing member and joins with the end (12a, 12b) of the drive gear. It can clearly be seen in FIG. 6j that the both ends (12a; 12b) of the drive gear are carved such that the end of the side cover (31b, 31d) can pass through. The end of the drive gear (12a) that is fixed into one connection point (29) of the mouthpiece cover has a hole (12c) at the center. In addition, each of the connection points (29, 30) itself is a hole in shape (FIG. 6b). Therefore, the end of the drive gear (12a) is fixed into the connection point (29) of the mouthpiece cover while the extension part (33c) present at the centre of the inside surface of the protective cover is fixed into both the hole (12c) at the centre of said end of the drive gear and the connection point of the mouthpiece cover.

Figure 7A:
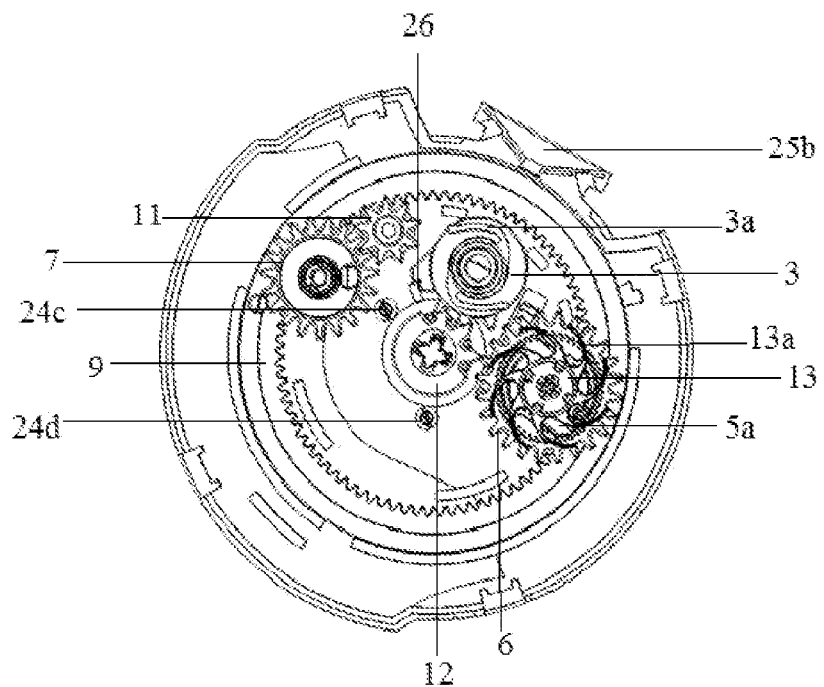
FIGS. 7*a* and 7*b* are cross-sectional views of the engagement of the gears composing the gear mechanism with each other in the inhaler according to the present invention.
Figure 7B:
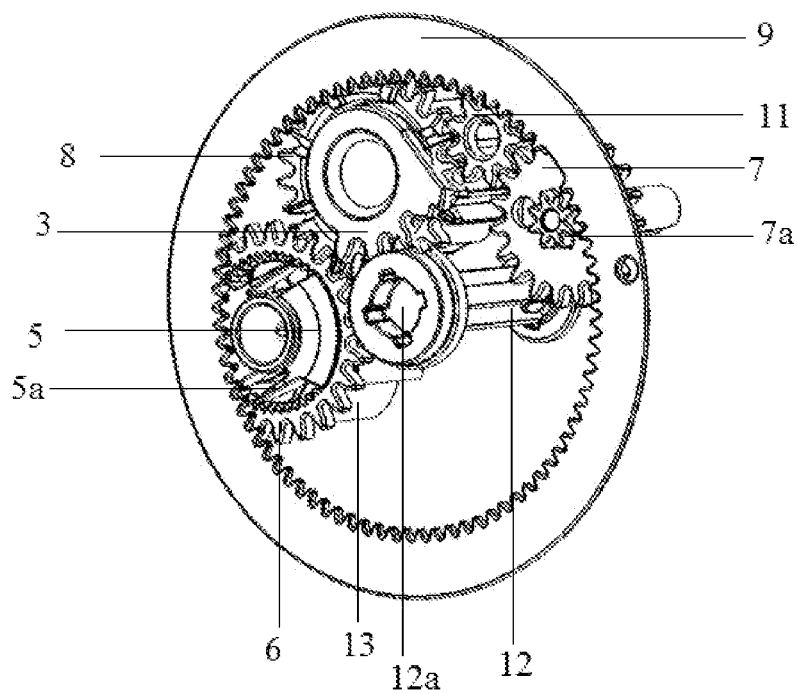
Figure 7C:
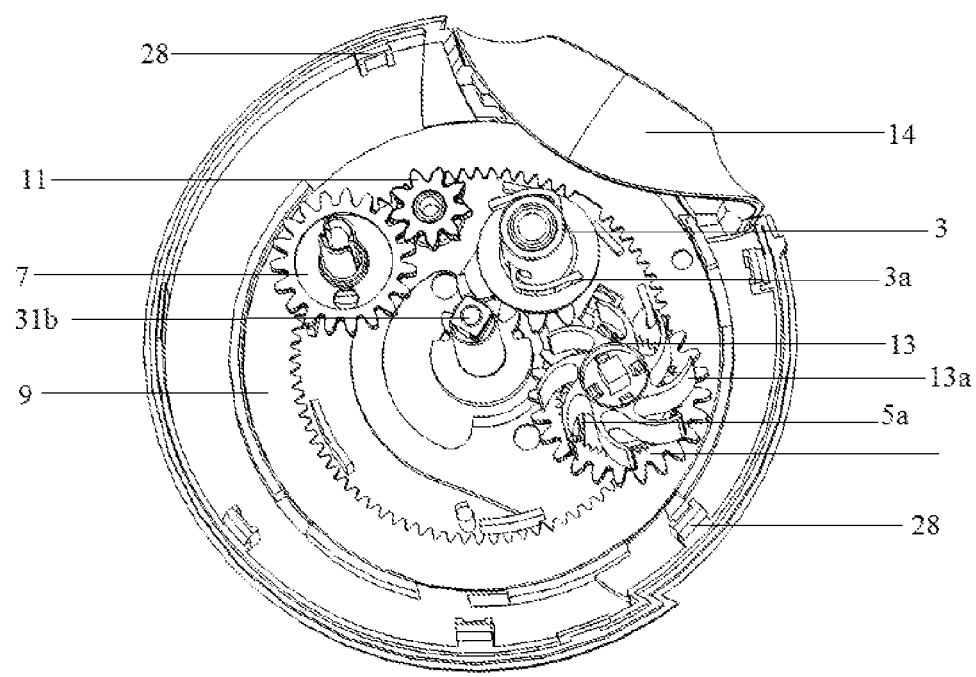
FIG. 7*c* is a cross-sectional view of the engagement of the gears composing the gear mechanism in the inhaler of the present invention.
Figure 7D:
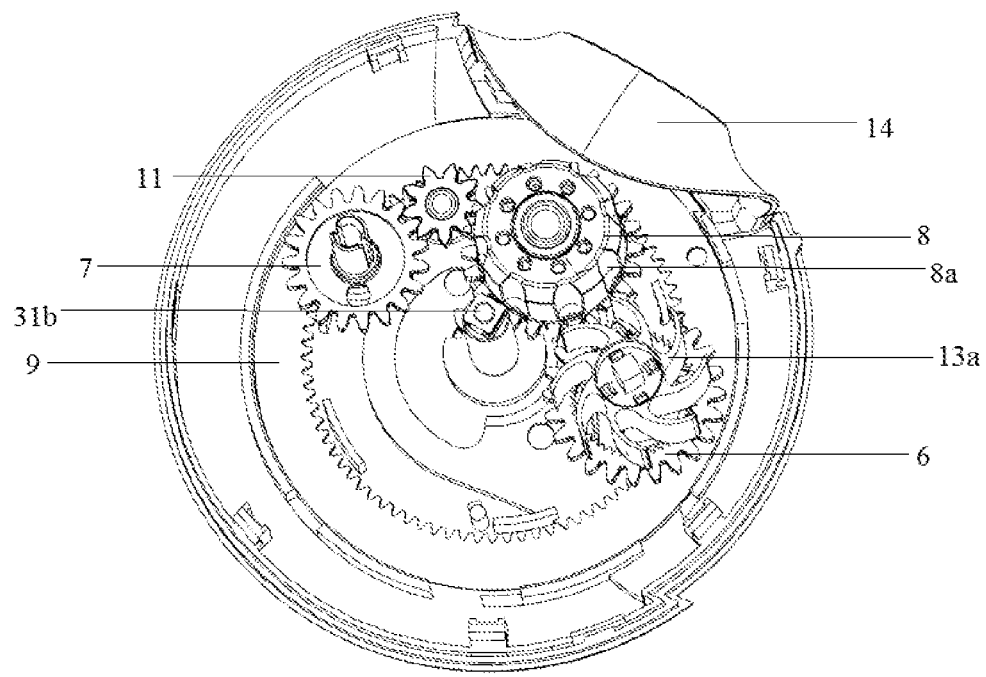
FIG. 7*d* is another cross-sectional view of the engagement of the gears composing the gear mechanism in the inhaler of the present invention.
Figure 7E:
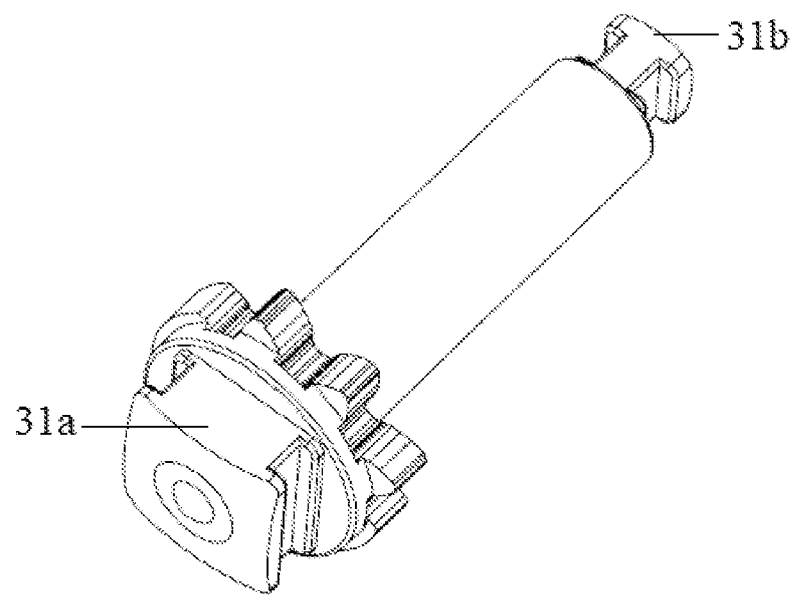
FIGS. 7*e* and 7*f* are perspective views of the drive gear of the inhaler according to the invention.
Figure 7F:
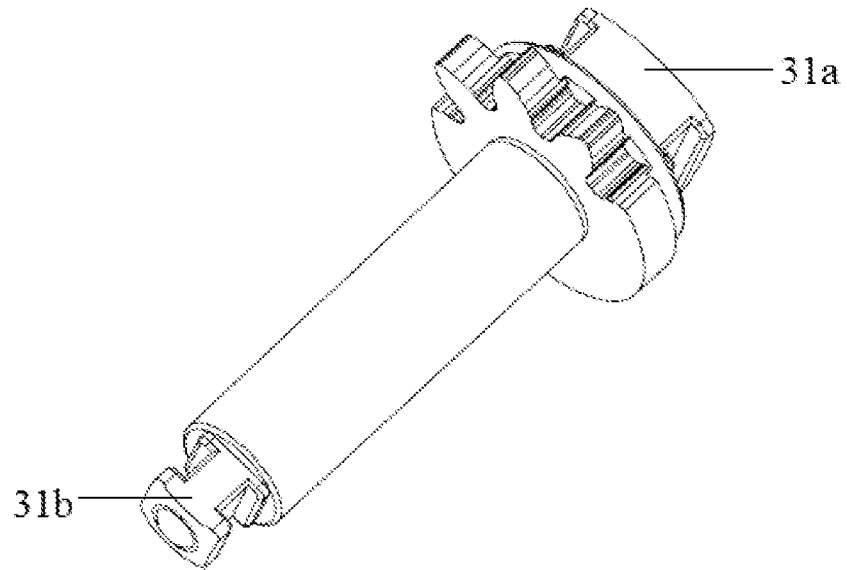

The shape of one connection point (29) of the mouthpiece cover is different from the shape of the second connection point (30) of the mouthpiece cover as well as the shape of the end of the drive gear (12a) that is connected with one connection point (29) of the mouthpiece cover is different from shape of other end of the drive gear (12b) (FIGS. 6b, 7f and 7g).

Each end of the side covers (31d, 31b) passes through one of the connection points (29, 30) of the mouthpiece cover and it is received in the recess in one end (12b, 12a) of the drive gear, thus it provides to tightly and stably interconnect the mouthpiece cover (2) with the drive gear (12). It is provided that the mouthpiece cover (2) synchronizes with the drive gear (12) as the connection point (29, 30) of the mouthpiece cover which has a matching shape with the ends (31d, 31b) of the side covers that passes through it on both sides of the device and the end (12b, 12d) of the drive gear that it communicates with are on the same component.

As is seen from FIGS. 6a through 6j, and 7h, the shapes of the ends (31b; 31d) of the side covers that are received in the carved parts on the ends of the drive gear and the shapes of the connection points (29, 30) of the mouthpiece cover are not identical since the two ends (12a, 12b) of the drive gear are not identical.

The mouthpiece cover (2) rotates by the same angle each time it is switched from the first position to the second position on the path restricted by the protrusions (29a, 29b, 30a, 30b) on the upper and the lower housing members (4a, 4b). The rotational angle of the mouthpiece cover (2) varies depending on the shape and the size of the device but is a fixed value between 30° and 160°. This angle is adjusted according to the shape and the size of the device such that the indexing wheel (8) having 8 recesses (8a) rotates 45 degrees in response to each actuation of the device. The mouthpiece cover (2) rotates by the same angle on its two ends in response to each actuation of the device and this rotational movement of the mouthpiece cover (2) is accurately transmitted to the indexing wheel (8) by the indexing ratchet wheel (3) because of the drive gear (12) which is tightly attached to the mouthpiece cover (2) and the indexing wheel is provided to rotate 45° each time the device is triggered.

Figure 2C:
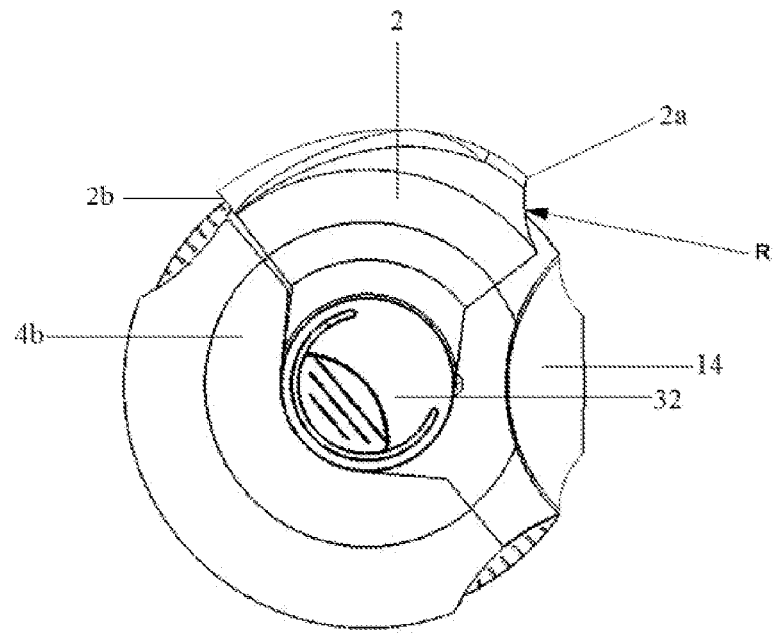
FIG. 2c is a front view of the inhaler according to the present invention.

The mouthpiece cover (2) can be rotated by holding from the front end (2a) or back end (2b) of its with the help of the thumb. Therefore, the front end (2a) or the back end (2b) of the mouthpiece cover (2) is in contact with the patient's finger while it is moved manually. According to FIG. 2c, only the front end (2a) of the mouthpiece cover (2) of the inhaler is carved such that it matches with the shape of the thumb so as to provide the mouthpiece cover (2) to be rotated easily and rapidly while the back end (2b) of the mouthpiece cover is not carved. However, it is probable that both the front end (2a) and the back end (2b) of the mouthpiece cover are carved. The shape of the carved part in the front end (2a) of the mouthpiece cover resembles to the shape of the thumb for the thumb to be placed in this carved part exactly in order to rotate the mouthpiece cover. Thus, the carved part of the front end (2a) of the mouthpiece cover illustrated in FIG. 2c is in the shape of the arc of the circle which has a radius (R) in the range of 30 mm to 40 mm, preferably in the range of 32.5 mm to 37.5 mm. In more detail, the carved part (2a) in the front end of the mouthpiece of the device shown in FIG. 2c is in the shape of the arc of 45° of said circle.

The mouthpiece cover that triggers the gear mechanism of the device can be found in two positions. When the mouthpiece cover is in the first position, the mouthpiece cover resides on the protruding part on one end of the rotational path. When the first position is on, the mouthpiece cover is completely covered and the device is in standby mode. When the mouthpiece is in the second position, it resides on the protruding part on the other end of the rotational path and one dose of the dry powder medicament becomes ready for inhalation upon the actuation of the device.

According to the present invention, there preferably exists a finger tab on the device cover. The word "finger tab" refers to the component that enables the patient to slide the cover comfortably.

Each gear of the gear mechanism in the device according to the present invention directly or indirectly engages with each other. The drive gear, which is one of the components of the gear mechanism, provides the mouthpiece cover to trigger the gear mechanism in such a way that the two ends of the drive gear which engage with the recessed parts on the inside face of the mouthpiece cover through a male-female connection enable an inside lock connection to be provided between the mouthpiece cover and the drive gear. One of the recesses on the inside surface of the mouthpiece cover engages with the one end of drive gear while the other recess on the inside surface of the mouthpiece cover engages with the other end of the drive gear and the connection, that is provided between the each end of the drive gear and the corresponding recess on the inside surface of the mouthpiece cover, is a male-female connection.

As regards the other components of the gear mechanism, in each actuation of the device, the constant-angle rotational movement of the cover is transmitted by the indexing ratchet wheel which interlocks with the indexing wheel via the drive gear. The indexing wheel synchronizes with the indexing ratchet wheel when the mouthpiece cover is switched from the first position to the second position. The gear of the indexing wheel is engaged with the winding wheel gear and the pinion gear and the rotation of the indexing wheel gear causes them to move as well. The mechanism wheel engages with the winding wheel gear via its arms. The counter gear that engages with the small gear under the base gear rotates by means of the base gear that engages with the pinion gear and counter gear with movement of the mouthpiece cover. Therefore, with the rotation of the indexing wheel, both the lid sheet of the blister package is provided to be coiled on the wings of the winding wheel as the winding wheel is rotated by the mechanism wheel that engages with the winding wheel gear, and the counter gear that engages with the small gear under the base gear rotates by means of the base gear that engages with the pinion gear. After the counter gear is rotated, the new number of unused blister pockets can be seen through the display aperture. According to the present invention, the mouthpiece cover triggers the gear mechanism via the drive gear. Therefore, the rotation of the mouthpiece cover has to be transmitted to the drive gear precisely in order to prevent uncontrolled dosing resulting from the mispositioning of the blister package when the device is triggered. In an inhalation device comprising a blister package which has a gear mechanism triggered by the mouthpiece cover, it is required that the rotation of the mouthpiece cover is transmitted to the gear mechanism with minimum margin of error for the blister package to be accurately positioned.

According to the present invention, the mouthpiece cover, whose recessed parts on the inside surface of said mouthpiece cover engage with the two ends of the drive gear through a male-female connection such that the inside lock connection is provided between the mouthpiece cover and the drive gear. In each actuation of the inhalation device, the gear mechanism is triggered by the rotational movement of said mouthpiece cover from the first position to the second position along the rotational path restricted on both ends by the protruding parts on the upper and the lower housing members to provide the blister package to be advanced. In each actuation of the device, the constant-distance path that the protrusions of the upper and the lower housing members define allows said mouthpiece cover to be rotated by a fixed angle. Accordingly, because of the inside lock connection provided between the mouthpiece cover and the drive gear, in each actuation of the inhalation device, only rotation of said mouthpiece cover from the first position to the second position on the constant-distance path guarantees that the blister package is advanced by the same distance and the opened blister is at accurate position so that the sufficient amount of the dry powder formulation contained in the opened blister can be inhaled. In addition to this, the patient can make sure about whether the blister is opened completely by controlling the position of the mouthpiece cover on the constant-distance path. In other words, if the mouthpiece cover is in the second position wherein it resides on the protruding part on the other end of the constant-distance rotational path, the patient makes sure that one blister is completely opened and one dose of the dry powder medicament contained in the opened blister becomes ready for inhalation; if the mouthpiece cover is between the first position and the second position, the patient makes sure about that one blister is not completely opened.

Two ends of the drive gear has been designed such that they form an inside lock connection with the mouthpiece cover. The inside lock connection between the two ends of the drive gear is formed preferably by male-female connections on the both sides. According to the present invention, due to this inside lock connection, the rotational movement of the mouthpiece cover is transmitted to the gear mechanism with minimum margin of error for the blister package to be accurately positioned. Therefore, the rotational movement of the mouthpiece cover has to be transmitted to gear mechanism exactly in order to prevent uncontrolled dosing resulting from the mispositioning of the blister package when the inhalation device is actuated. The mouthpiece cover and the drive gear synchronize with maximum ±0.01% margin of error thanks to the inside lock connection between the mouthpiece cover and the drive gear. This rate of margin of error resulting from the connection between the mouthpiece cover and the drive gear enables each blister pocket from the first one to the last to be opened completely because the precise positioning of the blister package is based on exact transmission of the movement of the mouthpiece cover to the other components in an inhalation device triggered by the mouthpiece cover. Accordingly, the drive gear, which has an inside lock connection with the mouthpiece cover, transmits the movement of the mouthpiece cover that rotates by the same angle in each inhalation to the indexing wheel via an indexing ratchet wheel interlocked into an indexing wheel and enables the blister package to be indexed properly and the opened blister pocket to be positioned accurately in the device pertaining to the present invention.

According to the present invention, the indexing wheel can be another component of the gear mechanism. As a result of the transmission of the rotation of the mouthpiece cover to the gear mechanism via the drive gear with ±0.01% margin of error, the blister pockets are received in the recesses of the indexing wheel, the blister package is indexed properly and the opened blisters are accurately positioned. The recesses of the indexing wheel match with the shape of the blister package. Blister pockets of the blister package are received in these recesses while the indexing wheel rotates. The rotation angle of the indexing wheel depends on the number of the recesses of the indexing wheel. In each actuation of the inhalation device, the indexing wheel can be rotated by an angle of 15° to 120°. According to the invention, there are preferably 8 recesses of the indexing wheel. Therefore, the indexing wheel is supposed to rotate 45 degrees when the device is actuated for the blister to be positioned accurately. In the device pertaining to the present invention, the rotational movement of the mouthpiece cover which is fixed at a value between 30° and 160° is transmitted to the indexing wheel with ±0.01% margin of error owing to the connection between the mouthpiece cover and the drive gear whenever the device is actuated. Therefore, the indexing wheel rotates 45 degrees whenever the device is actuated. As the indexing wheel rotates 45 degrees whenever the device is actuated, the blister package is accurately positioned and controlled dosing of the medicament in dry powder from is provided.

At least one component may be situated on the lower housing member and serves as a stopper interlocks with the tooth of at least one of the gears of the gear mechanism and stabilizes the gear in a suitable position in order to prevent backward rotation of the blister package and enables it to be precisely positioned. While the stopper can hinder the rotation of any gear of the gear mechanism, it preferably hinders the rotation of the indexing ratchet wheel interlocked in the indexing wheel. The stopper can be anywhere suitable in the lower housing member and have any shape.

The counter gear in the device pertaining to the present invention may display the number of the unused blister pockets remained in the device. In response to the actuation of the device by the mouthpiece cover, the mouthpiece is uncovered, the blister package is indexed and one dose of the dry powder medicament is prepared for inhalation while the counter gear rotates as well. Thus, the movement of the mouthpiece cover leads to the mouthpiece being exposed; one dose of the dry powder medicament to be ready for inhalation after the blister pocket is opened as well as providing the counter gear to rotate and display the new value of the remaining unused blister pockets through the display aperture.

On the counter wheel, there exist numerals equal to the number of the blister pockets present in the device and they are spaced by equal angles. In a device comprising 60 doses, the angle between the numerals is approximately 5 degrees. The counter gear rotates as a result of the reflection of the rotation of the indexing wheel gear via the pinion gear and the base gear. In response to the each actuation of the device, rotation of the indexing wheel by the same angle each time due to the accurate transmission of the movement of the mouthpiece cover to the gear mechanism via the drive gear results in the rotation of the counter gear approximately by the same angle as well, and each numeral on the counter wheel is clearly seen through the display aperture on the upper housing member. Therefore, the patient is sure about the number of the unused blister pockets remaining in the device.

The inhaler according to the present invention comprises a blister package composed of a plurality of blister pockets each of which comprises medicament in dry powder form and which are spaced at equal intervals. The blister package carries the medicament in dry powder form in one-dose portions and it is preferably a blister strip and it is preferably peelable. The blister pockets comprised in the blister package are spaced in equal intervals and each of them carries one dose of the medicament in dry powder form. While the blister package is indexed on the indexing wheel, the beak on the housing peels the blister. Therefore, one dose dry powder medicament becomes ready for inhalation after the blister package is peeled open in each actuation of the device.

According to another aspect, the blister opened by the beak may be situated immediately under a manifold. The airflow that enters the device through at least one air inlet on the upper housing member entrains the dry powder medicament in the opened blister pocket via the manifold to the mouthpiece and enables the delivery of said medicament to the patient. The air inlet on the upper housing member that allows the entry of air can be in any suitable shape and size that enables external air to enter the device easily and at a convenient speed.

The air inlet that the external air flow passes through is designed not to be close where the patient holds the device in order not to prevent air flow. Furthermore, in order to deliver the required amount of the dry powder medicament in the opened blister to the patient, the air inlet is designed such that it allows the entry of the airflow through the air inlet at a convenient angle.

The lid and the base sheets constituting the blister package preferably consist of a plurality of layers. These layers are preferably chosen from a group comprising polymeric layers that are made of polymeric substances, aluminum foil and fluoropolymer film.

According to the present invention, the lid and base sheets forming the blister package are sealed very tightly by at least one of the methods preferably comprising cold formed bonding, hot metal bonding, hot metal welding, radio frequency welding, laser welding or ultrasonic welding in order to provide impermeability, more preferably by cold formed bonding method. Since these cold formed bonding methods can be carried out at lower temperatures than hot sealing methods, they are the most appropriate methods to use in the case that the medicament carried in the blister is heat sensitive.

Fluoropolymer film is a polymeric film which is used in blister packs and provides an excellent moisture barrier. This chemically inert polymeric film does not cause any change in the taste of the formulation when it is in contact with the dry powder formulation. In addition, it easily constitutes a layered structure with the other polymeric layers which are composed of various polymers. It is appropriate to be transacted with heat.

For preserving the stability of the dry powder formulation stored in the blister package, preferably at least one of the polymeric layers comprises at least one desiccant agent including silica gel, zeolite, alumina, bauxite, anhydrous calcium sulfate, activated carbon and clay which has the property of water absorption in order to decrease gas and moisture permeability of the layer.

In order to provide high moisture and gas protection, aluminum foil can be used in the lid and base sheets of blister packs. This aluminum foil must be thick enough to provide the desired protection for the stability of the moisture sensitive dry powder formulation stored in the blister cavity and it may be preferably in the range of 5 to 80 μm, more preferably in the range of 15 to 65 μm.

The polymeric layers in the lid and the base sheets of the blister pack mentioned in the present invention are made of the same or different polymers. The thickness of these polymeric layers varies according to the type of the polymeric substance used and its properties and are preferably in the range of 5-100 μm, more preferably in the range of 15-60 μm.

The polymers composing the polymeric layer are preferably selected from thermoplastics such as polyethylene, polypropylene, polystyrene, polyolefin, polyamide, polyvinyl chloride, polyurethane or synthetic polymers.

The blister pockets in the blister package can be in any appropriate shape. The plurality of blister pockets spaced at equal intervals on the base sheet of the blister package can be in the same or different shape, structure or volume.

Figure 2D:
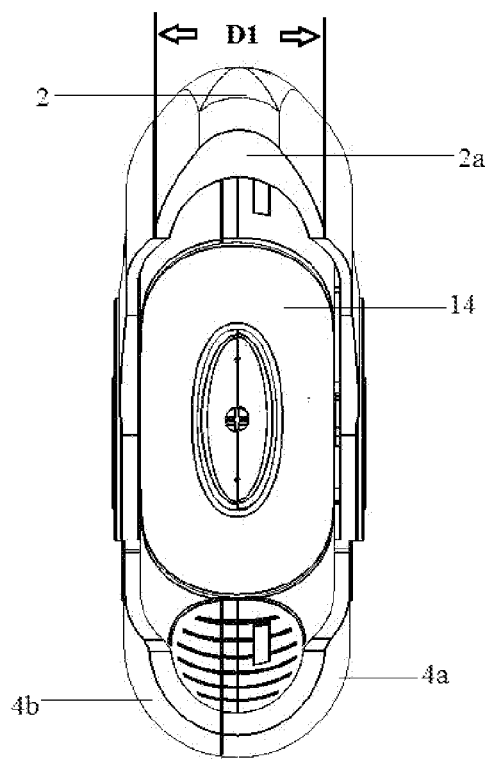
FIG. 2d is a lateral view of the inhaler according to the present invention.

In addition, another variable contributing to the carved part in the front end (2a) of the mouthpiece cover to match with the shape of the thumb is the width of the mouthpiece cover (2) illustrated as D1 in FIG. 2d. For the thumb to be able to grip the cover and impose force, a particular part has to be in contact with the carved part in the front end (2a) and the back end (2b) of the mouthpiece cover. To this end, D1 distance is in the range of 10 mm to 20 mm, preferably in the range of 11 mm to 16 mm.

Figure 8:
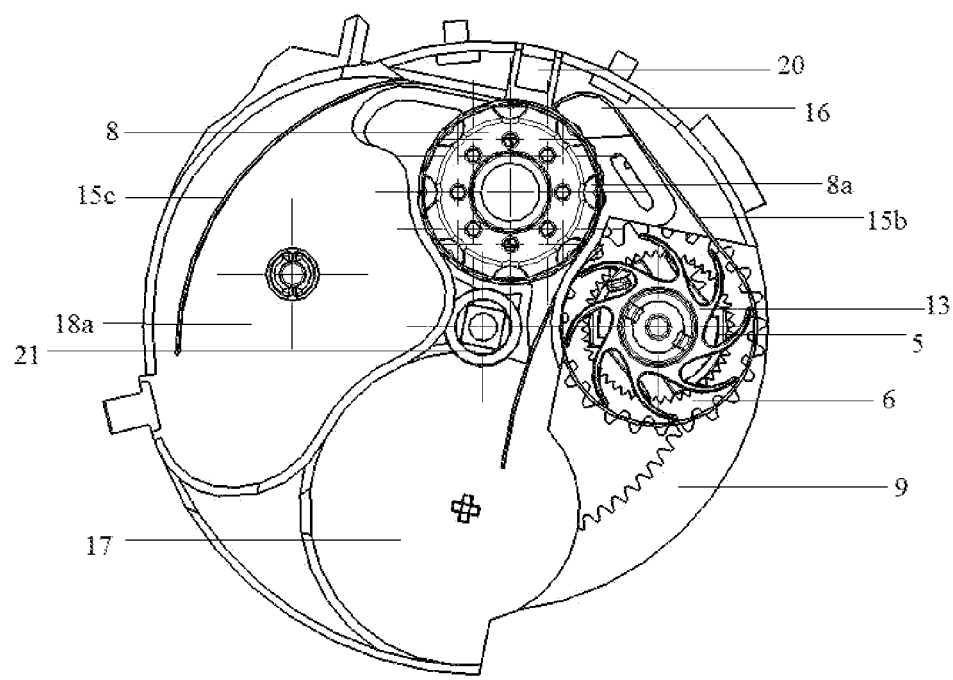
FIG. 8 is a cross-sectional view of the blister package delaminating in course of operation of the inhaler according to the present invention.

There are 8 recesses (8a) on the indexing wheel displayed in FIG. 2a and the indexing wheel (8) rotates 45° each time for the blisters received in these recesses to be able to be positioned accurately. The blister package (15) is indexed by the 45° rotation of the indexing wheel (8) in response to each actuation of the device and is peeled by the beak (16) so one dose of the dry powder medicament becomes ready for inhalation when one blister pocket is opened. As seen in FIG. 8, the lid sheet (15b) that is peeled away by the beak (16) and the base sheet (15c) of the blister package (15) are enclosed in separate compartments. The lid sheet (15b), which provides impermeability of the blister package, passes over the beak (16) and tightly coils on the wings (13a) of the winding wheel. The base sheet (15c) with blister pockets (15a), each of which comprises one dose of the dry powder medicament, is accumulated in the separated compartment (18a) in the housing (10). In response to each actuation of the inhaler (1), one dose of the dry powder medicament becomes ready for inhalation after one blister pocket (15a) is opened; the air which enters the device through the air inlet (22) upon the inhalation of the patient entrains the dry powder medicament to the mouthpiece and provides to deliver it to the patient.

There is at least one stopper (26) in the lower housing member displayed in FIG. 6a in order to provide the opened blister in the blister package (15) which is indexed by the indexing wheel (8) so as to be positioned accurately. This stopper (26) engages with the tooth of at least one gear and provides the position of this gear to stay immovable and the opened blister to be accurately positioned. This stopper (26) can be any suitable shape and size according to the structure of the gear it stops.

Figure 6I:
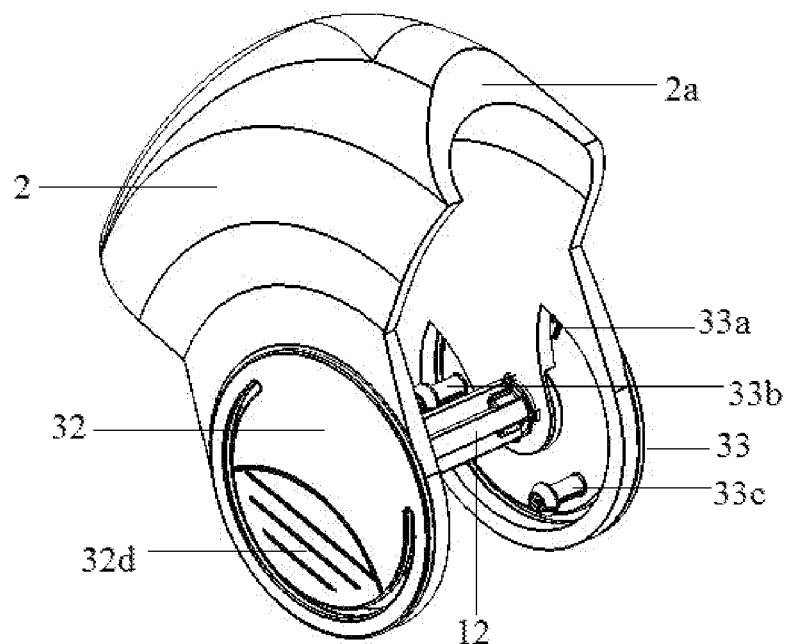
FIG. 6*i* is a cross-sectional view of the communication between the mouthpiece cover, the drive gear and the stabilizing resilient covers in the inhaler according to the invention.
Figure 6J:
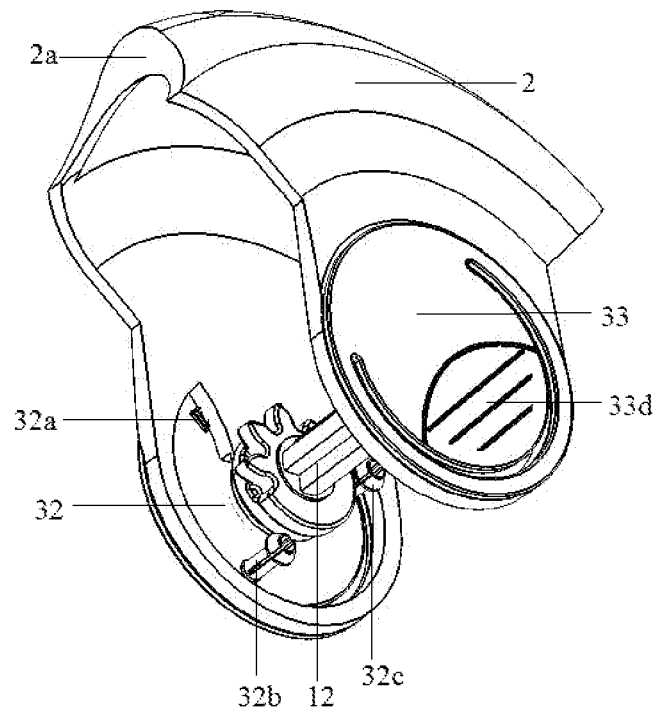
FIG. 6*j* is a cross-sectional view of the communication between the mouthpiece cover, the drive gear and the stabilizing resilient covers in the inhaler according to the invention.
Figure 7G:
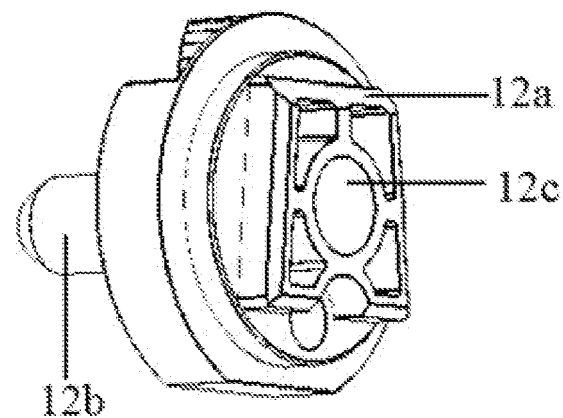
FIG. 7*g* is a perspective view of the drive gear of the inhaler of the invention.
Figure 7H:
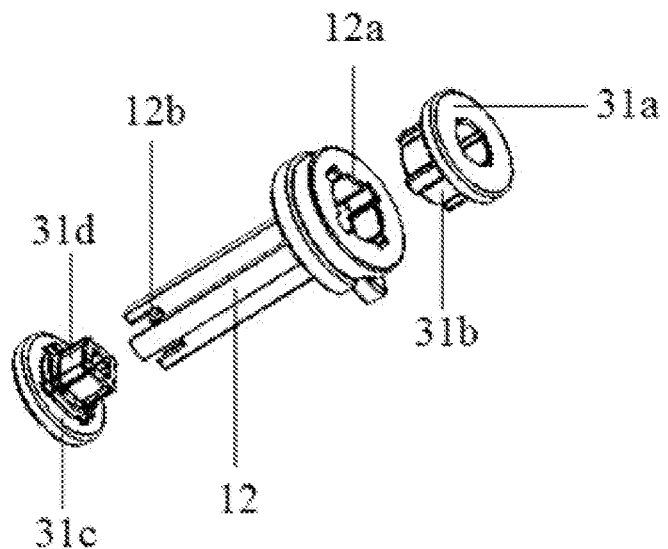
FIG. 7*h* is an exploded view of the communication between the drive gear and the side covers in the inhaler according to the invention.

There is one stabilizing resilient cover (33; 32) on each connection point (29; 30) of the mouthpiece and on each side cover (31c; 31a), as displayed in FIGS. 2a, 6a, 6h-6j and 5i. When the mouthpiece cover (2) is in the first position, the pawls (32a, 33a) under the stabilizing resilient covers, which are on the connection points (29, 30) of the mouthpiece, interlock with the mouthpiece cover (2) on both sides as clearly seen in FIGS. 6i and 6j. The pawl (33a) under the stabilizing resilient cover that is on the first connection point (29) interlocks with the mouthpiece cover on one side (FIG. 6i). Identically, the pawl (32a) under the stabilizing resilient cover that is on the second connection point (30) of the mouthpiece cover interlocks with the mouthpiece cover (2) on the other side (FIG. 6j). Thus, these pawls (32a, 33a)

under the stabilizing resilient covers prevent the movement of the mouthpiece cover (2) by interlocking with it on both sides.

The extensions (32b, 32c, 33b, 33c) under the stabilizing resilient covers pass through the apertures (23c, 23d, 24c, 24d) on the upper and the lower housing members illustrated in FIGS. 5a and 5b and provide the stabilizing resilient covers to remain stable. Namely, the extensions (33b, 33c) under the stabilizing resilient cover that is on the first connection point (29) of the mouthpiece cover pass through the apertures (23c, 23d) on the upper housing member and provide one of the stabilizing resilient covers (33) to be stably joined with the device. Identically, the extensions (32b, 32c) under the stabilizing resilient cover on the second connection point (30) of the mouthpiece cover pass through the apertures (24c, 24d) on the lower housing member and provide one of the stabilizing resilient covers (32) to be stably joined with the device as clearly illustrated in FIG. 5i.

Before the inhalation, the resilient parts (32d, 33d) of each stabilizing resilient cover illustrated in FIGS. 6i and 6j are pressed on for raising the pawls (32a, 33a) and releasing the mouthpiece cover (2) in order to actuate the gear mechanism of the device to prepare one dose of dry powder medicament before inhalation. Therefore, the gear mechanism of the device is actuated and one blister pocket (15a) is opened for one dose of the dry powder medicament to be ready for inhalation when the resilient parts (32d, 33d) of the stabilizing resilient covers are pressed on and the mouthpiece cover (2) is switched from the first position to the second position simultaneously. The necessity to press on the resilient parts (32d, 33d) of the stabilizing resilient covers so as to actuate the gear mechanism preclude the consequences which may result from accidental and inadvertent actuations of the gear mechanism.

Figure 4I:
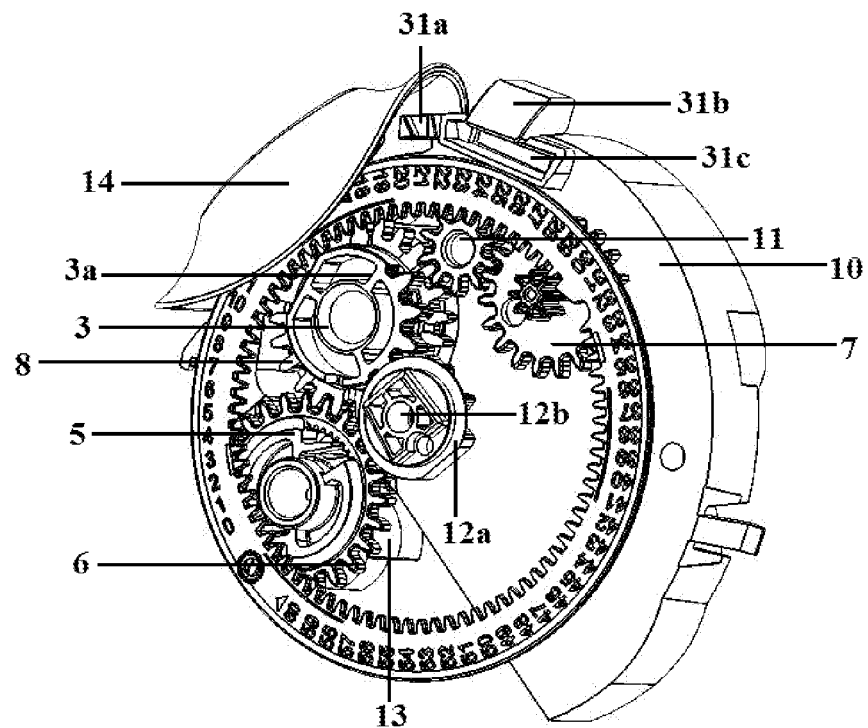
FIGS. 4i and 4j are perspective views of the housing and the gear mechanism of the inhaler of the invention.
Figure 4J:
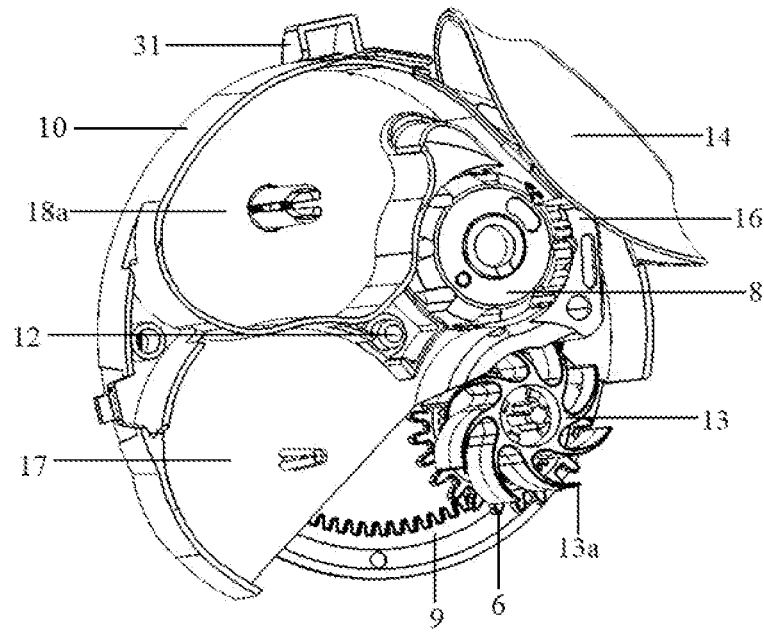
Figure 10A:
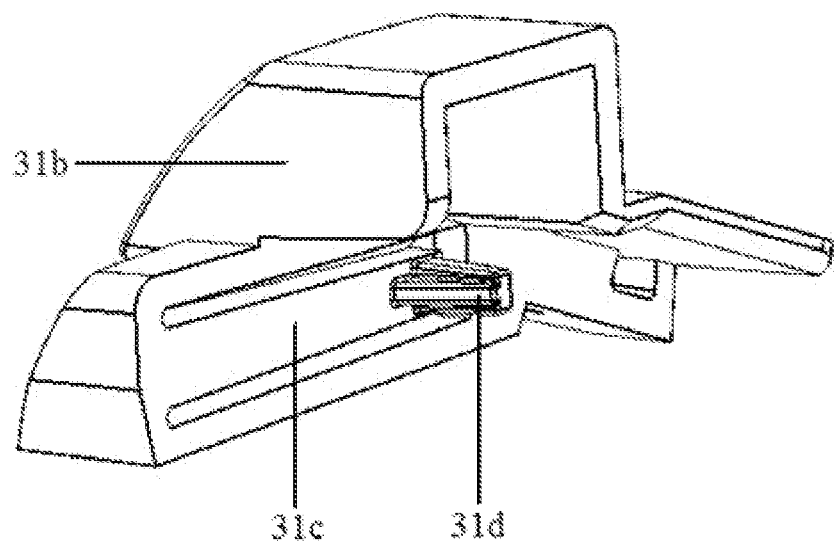
FIGS. 10*a* and 10*b* are perspective views of the stopper consisting of the pawl, the pressing button, and the supporting member used in the inhaler of the present invention.
Figure 10B:
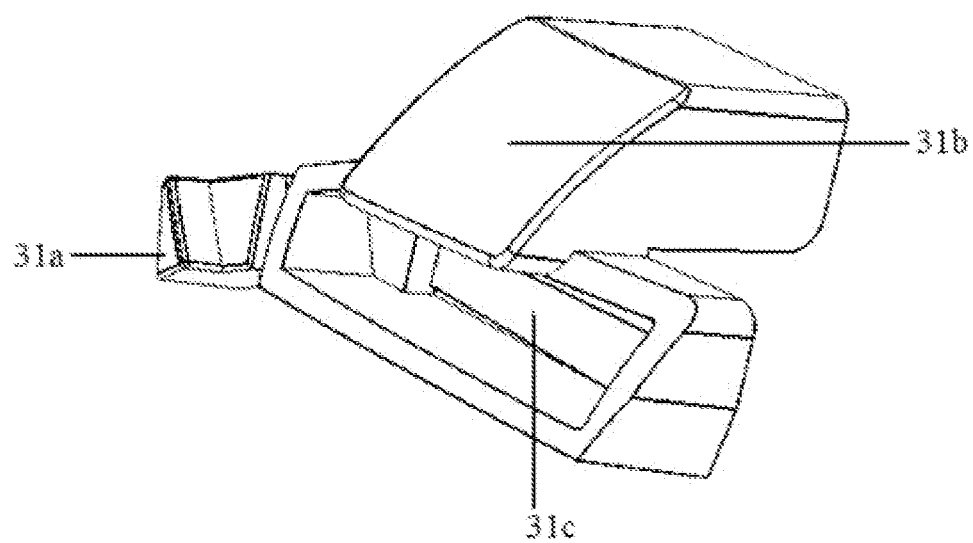

The inhaler (1) of the present invention has a stopper (31) that is situated between the lower housing member (4b) and the housing (10) as engaging with the two holes on the lower housing member (4b) (FIGS. 5d and 6a). The stopper is shown in FIGS. 10a and 10b. This stopper (31) consists of a pawl (31a), a pressing button (31b), and a supporting part (31c). Each of the pawl (31a) and the pressing button (31b) situated in one hole of the lower housing member (4b) and is shown from the outside as the supporting part (31c) is situated at the inside of the inhaler and is not shown from the outside (FIGS. 4i and 6a). For actuation of the inhaler, the mouthpiece cover (2) is switched from the first position to the second position over the rotational path. However, the pawl (32a) is engaged to the recess part (2c) on inside surface of the mouthpiece cover (2) to prevent the movement of the mouthpiece cover (2) when the mouthpiece cover (2) is in the first position in which the mouthpiece (14) is completely covered. Since the pressing button (31b) moves synchronously with the pawl (31a), when the pressing button (31b) is pressed, the pawl (31a) is advanced forward inside of the inhaler and disengaged from the mouthpiece cover (2). After the pawl (31a) is disengaged from the mouthpiece cover (2), the mouthpiece cover (2) can be rotated from the first position to the second position to actuate the inhaler.

Because of the supporting part (31c) of the stopper, there is no need for a spring to enable the pressing button (31b) to be pressed. There is an end (31d) that is integrated with the supporting part and leans the housing of the inhaler. When the pressing button is pressed, the supporting part springs over the end of said supporting part (31d) and both of the pressing button (31b) and the pawl (31a) are advanced forward inside of the inhaler.

Figure 11:
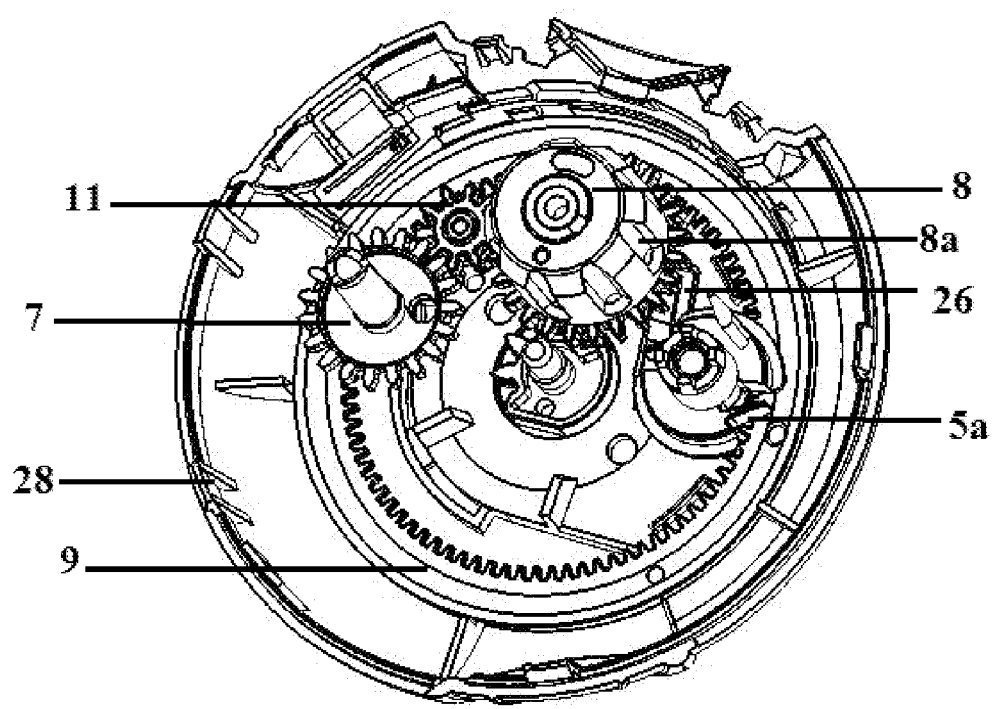
FIG. 11 is a perspective view of the connection between the indexing wheel and another stopper used in the inhaler of the invention.

The inhaler has another stopper (26) in the lower housing member (4b) in order to provide the opened blister in the blister package (15) which is indexed by the indexing wheel (8) to be positioned precisely. FIGS. 7a, 7b, and 11 show that the stopper (26) interlocks with the tooth of the indexing wheel (8) and hinders its rotation. The rotational movement of the mouthpiece cover (2) by the same angle each time the inhaler (1) is actuated is precisely transmitted to the indexing ratchet wheel (3) by the drive gear (12) that joins with one connection point (29) of the mouthpiece cover, and therefore the indexing wheel (8) which engages with the indexing ratchet wheel (3) is rotated by the same angle each time the inhaler (1) is actuated. The stopper (26) positioned in the lower housing member (4b) prevents backward movement of the blister package (15) which is indexed by the indexing wheel (8) that synchronizes with the indexing ratchet wheel (3) by keeping the position of the indexing wheel (8) stable and provides the blister package (15) to be precisely positioned.

As can be seen in FIGS. 7a through 7c, the indexing wheel (8) which synchronizes with the indexing ratchet wheel (3) is engaged with the winding wheel gear (6) and the pinion gear (11) and the rotation of the indexing wheel (8) causes the pinion gear (11) and the winding wheel gear (6) to rotate. Thus, both the peeled lid sheet (15b) of the blister package (15) which is indexed by the rotation of the indexing wheel (8) is tightly coiled on the winding wheel (13) engaging with the winding wheel gear (6) and also the counter gear (9) is provided to be moved by the pinion gear (11) and the base gear (7) as a result of the rotation of the indexing wheel (8).

Figure 9:
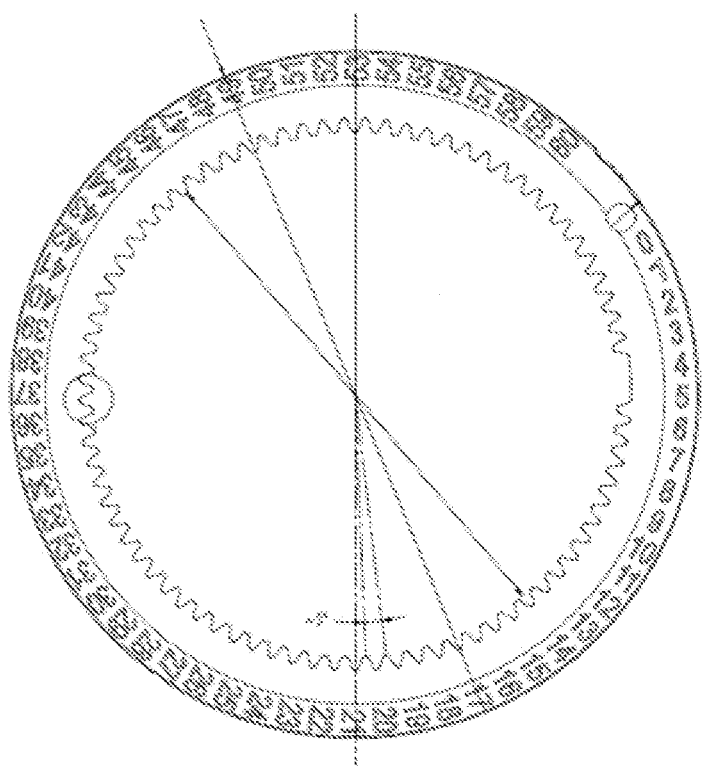
FIG. 9 is a perspective view of the counter gear used in the inhaler according to the present invention.

The rotation of the indexing wheel (8) is transmitted to the base gear (7) engaging with the pinion gear (11) by the pinion gear (11). The small gear which is under the base gear (7) as attached engages with the counter gear (9) (FIG. 7b). Thus, the movement of the indexing wheel (8) is transmitted to the counter gear (9) shown in FIG. 9 by the pinion gear (11) and the base gear. There are numerals incrementing from 1 to 60 in the counter gear displayed in FIG. 9. In response to each actuation of the device, the counter gear rotates approximately 5° and the number of unused blister pockets remained in the device are seen through the display aperture (4c) on the lower housing member (4b).

In use of the device described in FIGS. 1-12, the mouthpiece (14) is exposed when the mouthpiece cover (2) is slid from the first position to the second on the upper housing member (4a) and the lower housing member (4b); the gear mechanism is triggered by the drive gear (12) and one dose of dry powder medicament is prepared for inhalation; the counter gear (9) is indexed and the numeral seen through the display aperture (4c) on the lower housing member (4b) is incremented. After the inhalation is realized, the mouthpiece cover (2) is solely moved from the second position to the first position wherein the mouthpiece (14) is completely covered.

The medicament in dry powder form which is stored in blister cavities is manufactured according to the prior art. According to the present invention, the particle sizes of the active agents comprised in the dry powder medicament are smaller than 20 µm, preferably smaller than 10 µm.

The inhaler pertaining to the present invention has been designed so as to deliver the dry powder medicament used in monotherapy or combined therapy. The term "monotherapy" refers to inhalation treatments in which dry powder medicaments comprising a single active agent are used whereas the term "combined therapy" refers to inhalation treatments in which dry powder medicaments comprising more than one active agents are use used.

The dry powder medicament delivered via the device pertaining to the present invention comprises at least one excipient in addition to the active agent or agents. These excipients are generally chosen from a group comprising monosaccharides (glucose, arabinose, etc.), disaccharides (lactose, saccharose, maltose, etc.), oligo- and polysaccharides (dextran, etc.), polyalcohols (sorbite, mannite, xylite), salts (sodium chloride, calcium carbonate, etc.) or combinations thereof. According to the present invention, the medicament in dry powder form comprises lactose as the excipient. The medicament in dry powder form comprises fine or coarse excipients particles preferably having various particle size ranges in order to deliver the required amount to the lungs.

The active agent or the active agents comprised in the dry powder medicament which is stored in blister packages used in the device pertaining to the present invention can be selected from a group comprising cromolyns, anti-infectives, antihistamines, steroids, anti-inflammatories, bronchodilators, leukotriene inhibitors, PDE IV inhibitors, antitussives, diuretics, anticholinergics, hormones, xanthines and pharmaceutically acceptable combinations thereof.

The active agent comprised in the medicament in dry powder form delivered via the inhaler pertaining to the present invention is preferably selected from a group comprising tiotropium, oxitropium, flutropium, ipratropium, glicopironium, flunisolid, beclomethasone, budesonide, fluticasone, mometasone, ciclesonide, rofleponide, dexamethasone, montelukast, methylcyclopropane acetic acid, sodium cromoglicat, nedocromil sodium, Npropylene, teophylline, roflumilast, ariflo (cilomilast), salmeterol, salbutamol, formoterol, terbutaline, carmoterol, indacaterol, cetirizine, levocetirizine, efletirizine, fexofenadine and their racemates, free base, enantiomers or diastereomers and their pharmaceutically acceptable salts, solvates and/or hydrates or a combination of said active agents.

The device pertaining to the present invention is used in the administration of the medicament in dry powder form which is utilized in the treatment of respiratory diseases, particularly in asthma, chronic obstructive pulmonary disorder (COPD) and allergic rhinitis. Accordingly, the respiratory diseases include, but not restricted to, allergic or non-allergic asthma at any phases, acute lung injury (ALI), acute respiratory distress syndrome (ARDS), exacerbation of airways hyperactivity, bronchiectasis, chronic obstructive pulmonary including emphysema and chronic bronchitis, airways or lung diseases (COPD, COAD or COLD), pneumoconiosis, aluminosis, anthracosis, asbestosis, chalicosis, ptilosis, siderosis, silicosis, tabacosis and byssinosis. The device pertaining to the invention can be used in prophylactic or symptomatic treatment. In addition, the medicament in dry powder form which is preferably used in the symptomatic treatment of allergic asthma and COPD is administered to the patient via the device pertaining to the present invention.

What is claimed is:

1. An inhaler suitable for delivery of a medicament in dry powder form from a blister package (15) comprising a plurality of blister pockets (15a), each of which comprises the medicament and is spaced at equal intervals, the inhaler comprising:
    (a) a mouthpiece (14) enabling a patient to inhale the medicament,
    (b) a gear mechanism enabling the blister package (15) to be indexed and the medicament to become ready for inhalation,
    (c) a rotatable mouthpiece cover (2) covering the mouthpiece (14) and triggering the gear mechanism,
    (d) a drive gear (12) joined with the mouthpiece cover (2), and
    (e) a housing (10) situated between an upper housing member (4a) and a lower housing member (4b) enclosing the blister package (15) and the gear mechanism,
    wherein an inside lock connection is provided between the mouthpiece cover (2) and the drive gear by two ends (31a, 31b) of the drive gear (12) enabling the mouthpiece cover (2) to connect with the gear mechanism and engaging with recessed parts (30a, 29a) on the inside face of the mouthpiece cover through a male-female connection.

2. The inhaler according to claim 1, wherein the inhaler further comprises at least one stopper (26) in the lower housing member (4b).

3. The inhaler according to claim 2, wherein the at least one stopper (26) engages with the teeth of at least one gear and hinders its rotation.

4. The inhaler according to claim 3, wherein the stopper (26) hinders the rotation of an indexing ratchet wheel (3) in the gear mechanism.

5. The inhaler according to claim 4, wherein the stopper (26) engages with the teeth of the indexing ratchet wheel (3) and hinders its rotation in order to precisely position the blister package (15).

6. The inhaler according to claim 1, wherein the inhaler is an easy-grip, manual device suitable for delivery of the medicament.

7. The inhaler according to claim 1, wherein the housing (10) comprises a beak (16) that peels the blister package (15) and a manifold (20) through which the medicament in the blister pocket (15a) passes during inhalation before reaching the mouthpiece (14).

8. The inhaler according to claim 1, wherein the inhaler comprises a path restricted by protrusions (23a, 23b, 24a, 24b) on the upper (4a) and the lower (4b) housing members.

9. The inhaler according to claim 8, wherein the mouthpiece cover (2) is rotatable by sliding along the restricted path.

10. The inhaler according to claim 9, wherein the mouthpiece cover (2) rotates by a fixed angle in the range of 30° to 160° along a constant-distance path defined by the protrusion parts (23a, 23b, 24a, 24b) in response to actuation of the inhaler.

11. The inhaler according to claim 1, wherein the mouthpiece cover (2) can be in two positions,
    a first position wherein the mouthpiece cover (2) resides on protruding parts (23a, 24a) at one end of a rotational path, wherein the mouthpiece cover is completely covered and the inhaler is in standby mode;
    a second position, wherein the mouthpiece cover (2) resides on protruding parts (23b, 24b) at the other end of the rotational path, wherein one dose of the medicament is ready for inhalation.

12. The inhaler according to claim 1, wherein the inhaler further comprises a finger tab on the mouthpiece cover to move the mouthpiece cover easily.

13. The inhaler according to claim 1, wherein the gear mechanism comprises:
    (a) the drive gear (12) that actuates the inhaler by transmitting the constant-angle movement of the mouthpiece cover (2) to an indexing ratchet wheel (3);

(b) an indexing wheel (8) which synchronizes with the indexing ratchet wheel (3) and enables the blister package (15) to be indexed in use;

(c) a winding wheel gear (6) which moves a winding wheel (13) via a mechanism gear (5) upon rotation of the indexing wheel (8);

(d) a pinion gear (11) and (e) a base gear (7) that transmit the movement of the indexing wheel (8) to a counter wheel;

(f) a counter gear (9) which displays the number of the unused blister pockets (15a) remaining in the inhaler.

14. The inhaler according to claim 13, wherein components (a) through (f) directly or indirectly engage with each other.

15. The inhaler according to claim 13, wherein the indexing wheel (8) comprises 8 recesses (8a) which are components of the gear mechanism.

16. The inhaler according to claim 15, wherein the angles between the recesses (8a) are all equal and 45°.

17. The inhaler according to claim 15, wherein the shape of the recesses (8a) is the same shape as that of the blister pockets (15a).

18. The inhaler according to claim 13, wherein the rotation of the indexing wheel (8) by an angle of 45° in response to each actuation of the inhaler is provided by an inside lock connection between the mouthpiece cover (2) which rotationally moves at a fixed value in the range of 30° to 160° according to the shape of the inhaler.

19. The inhaler according to claim 13, wherein the counter gear (9) comprises numerals equal to the number of the blister pockets (15a) to be inserted for use.

20. The inhaler according to claim 19, wherein the numerals are increments from 1 to 60 equal to 60 blister pockets (15a) each containing a single dose of the medicament.

21. The inhaler according to claim 20, wherein the angles between the numerals on the counter gear (9) are of approximately 5°.

22. The inhaler according to claim 1, further comprising at least one air inlet (22) on the upper housing member (4a) to provide air flow.

23. The inhaler according to claim 1, wherein the blister package (15) is a blister strip.

24. The inhaler according to claim 23, wherein the blister strip is peelable.

25. The inhaler according to claim 23, wherein the blister package comprises a lid sheet (15b) and a base sheet (15c) comprising a plurality of layers.

26. The inhaler according to claim 25, wherein the layers are selected from the group consisting of polymeric layers, aluminum foil, and fluoropolymer film.

27. The inhaler according to claim 25, wherein at least one of the layers comprises a desiccant agent selected from the group consisting of silica gel, zeolite, alumina, bauxite, anhydrous calcium sulfate, activated carbon, and clay.

28. The inhaler according to claim 26, wherein the thickness of the aluminum foil is in the range of 5 to 80 µm.

29. The inhaler according to claim 28, wherein the thickness is in the range of 15 to 65 µm.

30. The inhaler according to claim 26, wherein the thickness of the polymeric layer is in the range of 5 to 100 µm.

31. The inhaler according to claim 30, wherein the thickness is in the range of 15 to 60 µm.

* * * * *